United States Patent
Wang et al.

(10) Patent No.: US 7,905,710 B2
(45) Date of Patent: Mar. 15, 2011

(54) SYSTEM AND METHOD FOR IMPROVED LOW FLOW MEDICAL PUMP DELIVERY

(75) Inventors: David T. Wang, Sunnyvale, CA (US); Peter J. Scaramuzzi, Morgan Hill, CA (US); Mansour A. Saleki, San Jose, CA (US); Robert P. Cousineau, Boston, MA (US); Kent D. Abrahamson, Morgan Hill, CA (US); Michael W. Lawless, Locust Grove, OK (US); Marwan A. Fathallah, Mundelein, IL (US); Brian A. Kidd, Seattle, WA (US); Robert R. Boyd, Jacksonville, FL (US); Howard L. Greene, Worthington, OH (US); Eric R. Navin, Columbus, OH (US); Lori E. Lucke, Eagan, MN (US); Benjamin T. Mullin, Lino Lakes, MN (US)

(73) Assignee: Hospira, Inc., Lake Forest, IL (US)

( * ) Notice: Subject to any disclaimer, the term of this patent is extended or adjusted under 35 U.S.C. 154(b) by 1015 days.

(21) Appl. No.: 11/510,106

(22) Filed: Aug. 25, 2006

(65) Prior Publication Data
US 2007/0058412 A1    Mar. 15, 2007

Related U.S. Application Data

(63) Continuation-in-part of application No. 10/810,123, filed on Mar. 26, 2004.

(51) Int. Cl.
F04B 49/00 (2006.01)
F04B 43/12 (2006.01)
G05D 7/00 (2006.01)
A61M 1/00 (2006.01)

(52) U.S. Cl. ............ 417/18; 417/53; 604/151; 604/153; 604/246; 700/282

(58) Field of Classification Search ............ 417/12, 417/18, 53; 604/151, 153, 246; 700/282
See application file for complete search history.

(56) References Cited

U.S. PATENT DOCUMENTS 3,985,467 A    10/1976    Lefferson
(Continued)

FOREIGN PATENT DOCUMENTS

EP    0 282 323    3/1988
(Continued)

OTHER PUBLICATIONS

S. Crystal Coley, et al, "Performance of three portable infusion-pump devices set to deliver 2 mL/hr", Amer. J. of Health System Pharmacy, vol. 54, Jun. 1997, pp. 1277-1280.

(Continued)

*Primary Examiner* — Charles G Freay
(74) *Attorney, Agent, or Firm* — Michael R. Crabb

(57) ABSTRACT

A medical pump with an improved continuity low flow delivery system and method for use with a pumping chamber, for example in a cassette, is disclosed. The pump includes a pump drive for exerting a force on the pumping chamber and a sensor for sensing the force/pressure exerted by the pump drive on the pumping chamber. The pump drive position sensor senses the position of the pump drive. The medical pump also includes a processing unit and a memory having a programming code adapted to calculate the rate of change of the sensed force/pressure values and determine whether the rate of change of the sensed force/pressure values meets a rate of change threshold. Once the rate of change threshold is met, the programming code is adapted to calculate a remaining pump drive travel value for determining how much farther the pump drive should travel before the end of an effective pump cycle. The programming code is further adapted to trigger one or more signals to drive the pump drive for the remainder of the effective pump cycle using the remaining pump drive travel value.

41 Claims, 9 Drawing Sheets

U.S. PATENT DOCUMENTS

| | | | |
|---|---|---|---|
| 4,078,562 A | | 3/1978 | Friedman |
| 4,308,866 A | | 1/1982 | Jelliffe et al. |
| 4,411,651 A | | 10/1983 | Schulman |
| 4,617,014 A | | 10/1986 | Cannon et al. |
| 4,741,736 A | | 5/1988 | Brown |
| 4,846,792 A | * | 7/1989 | Bobo et al. .................... 604/505 |
| 4,886,422 A | * | 12/1989 | Takeuchi et al. ................ 417/20 |
| 5,006,050 A | | 4/1991 | Cooke et al. |
| 5,116,312 A | | 5/1992 | Blankenship et al. |
| 5,174,472 A | * | 12/1992 | Raque et al. ....................... 222/1 |
| 5,292,306 A | * | 3/1994 | Wynkoop et al. ............. 604/505 |
| 5,399,171 A | | 3/1995 | Bowman et al. |
| 5,464,392 A | | 11/1995 | Epstein et al. |
| 5,482,438 A | | 1/1996 | Anderson et al. |
| 5,551,850 A | | 9/1996 | Williamson et al. |
| 5,658,133 A | | 8/1997 | Anderson et al. |
| 5,938,636 A | | 8/1999 | Kramer et al. |
| 5,957,890 A | | 9/1999 | Mann et al. |
| 6,259,587 B1 | | 7/2001 | Sheldon et al. |
| 6,267,559 B1 | | 7/2001 | Mossman et al. |
| 6,497,680 B1 | * | 12/2002 | Holst et al. .................... 604/153 |
| 2002/0013545 A1 | | 1/2002 | Soltanpour et al. |
| 2002/0018720 A1 | | 2/2002 | Carlisle et al. |
| 2002/0183693 A1 | | 12/2002 | Peterson et al. |
| 2003/0055375 A1 | | 3/2003 | Holst et al. |
| 2003/0091442 A1 | | 5/2003 | Bush et al. |
| 2004/0047736 A1 | | 3/2004 | Nose et al. |
| 2004/0120825 A1 | | 6/2004 | Bouton et al. |
| 2004/0247445 A1 | | 12/2004 | Nelson et al. |
| 2005/0021297 A1 | | 1/2005 | Hartlaub |
| 2005/0143864 A1 | | 6/2005 | Blomquist |
| 2005/0187515 A1 | | 8/2005 | Varrichio et al. |
| 2005/0214129 A1 | | 9/2005 | Greene et al. |
| 2005/0235732 A1 | | 10/2005 | Rush |
| 2005/0235733 A1 | * | 10/2005 | Holst et al. ..................... 73/1.16 |

FOREIGN PATENT DOCUMENTS

| | | |
|---|---|---|
| EP | 0 291 727 | 4/1988 |
| EP | 0 960 627 | 5/1999 |
| WO | 91/00113 | 1/1991 |
| WO | 98/04304 | 2/1998 |
| WO | 99/52575 | 10/1999 |
| WO | 00/13726 | 3/2000 |
| WO | 02/087664 | 11/2002 |
| WO | 2004/035115 | 4/2004 |
| WO | 2004/112579 | 12/2004 |
| WO | 2006/022906 | 3/2006 |

OTHER PUBLICATIONS

K. R. Dunster, et al, "Flow Continuity of Infusion Systems at Low Flow Rates", Anaesthesia and Intensive Care, vol. 23, No. 5, Oct. 1995, pp. 605-609.

Brian M. Ilfeld, et al, "Portable Infusion Pumps Used for Continuous Regional Analgesia: Delivery Rate Accuracy and Consitency", Regional Anesthesia and Pain Medicine, vol. 28, No. 5, Sep.-Oct. 2003, pp. 424-432.

Brian M. Ilfeld, et al, "Delivery Rate Accuracy of Portable Bolus-Capable Infusion Pumps Used for Patient-Controlled Continuous Regional Analgesia", Regional Anesthesia and Pain Medicine, vol. 28, No. 1, Jan.-Feb. 2003, pp. 17-23.

* cited by examiner

SYSTEM AND METHOD FOR IMPROVED LOW FLOW MEDICAL PUMP DELIVERY

CROSS-REFERENCE TO RELATED APPLICATIONS

This application is a continuation-in-part of U.S. patent application Ser. No. 10/810,123, filed Mar. 26, 2004.

FEDERALLY SPONSORED RESEARCH OR DEVELOPMENT

None.

TECHNICAL FIELD

The invention relates to medical pumps for delivering a substance, such as a fluid to a patient. In particular, the present invention relates to medical pumps which provide low flow delivery of a substance to a patient.

BACKGROUND OF THE INVENTION

Modern medical care often involves the use of medical pump devices to deliver substances, such as fluids and/or fluid medicine to patients. Medical pumps permit the controlled delivery of substances to a patient, and such pumps have largely replaced gravity flow systems, primarily due to the pump's much greater accuracy in delivery rates and dosages, and due to the possibility for flexible yet controlled delivery schedules.

A typical positive displacement pump system includes a pump device driver and a disposable fluid or pumping chamber, defined in various forms including but not limited to a cassette, syringe barrel or section of tubing. A disposable cassette, which is adapted to be used only for a single patient and for one fluid delivery round, is typically a small plastic unit having an inlet and an outlet respectively connected through flexible tubing to the fluid supply container and to the patient receiving the fluid. The cassette includes a pumping chamber, with the flow of fluid through the chamber being controlled by a plunger or pumping element activated in a controlled manner by the device driver.

For example, the cassette chamber may have one wall or wall portion formed by a flexible, resilient diaphragm or membrane that is reciprocated by the plunger and the driver to cause fluid to flow. The pump driver device includes the plunger or pumping element for controlling the flow of fluid into and out of the pumping chamber in the cassette, and it also includes control mechanisms to assure that the fluid is delivered to the patient at a pre-set rate, in a pre-determined manner, and only for a particular pre-selected time or total dosage.

The fluid enters the cassette through an inlet and is forced through an outlet under pressure. The fluid is delivered to the outlet when the pump plunger forces the membrane into the pumping chamber to displace the fluid. During the intake stroke the pump plunger draws back, the membrane covering the pumping chamber pulls back from its prior fully displaced configuration, and the fluid is then drawn through the open inlet and into the pumping chamber. In a pumping stroke, the pump plunger forces the membrane back into the pumping chamber to pressurize and force the fluid contained therein through the outlet. Thus, the fluid flows from the cassette in a series of spaced-apart pulses rather than in a continuous flow.

One of the requirements for a medical pump is that it is able to deliver precise volumes at precise delivery rates. Conventional pumps, in general, rely on nominal or empirical data to estimate the delivery volumes and delivery rates, and do not provide mechanisms for adjusting an actual delivery due to variations from this nominal or empirical data. This lack of adjustment during an actual delivery limits the accuracy and/or flow continuity of these pumps.

In addition, medical pumps are operated at low flow rates, such as below 1 mL/hr or less, the determination of when the medical pump is actually delivering a substance to a patient can be difficult. It has been found that sensed data can provide false indications that actual delivery of the substance, such as the flow of a fluid, is occurring. In fact, it has been determined that sensed data indicating that delivery of the substance has begun can actually be attributed to leakage or some other reason, as suggested by the sensed data, such as pressure, instead of the delivery actually beginning. Other potential difficulties occur when attempting to use traditional medical pumps at low flow rates, without using specialty items such as specialty neonatal cassettes. In particular, mechanical friction and/or electrical noise can also trigger false data indicating that the delivery has actually begun, inducing periods of no flow. This friction and/or noise can be attributed to many things, including but not limited to the cassette diaphragm, the plunger tip finish, and/or the plunger body O-rings to internal bearing pressure/force sensor flex bias.

Thus, it is a principal object of this invention to provide a medical pump and a method of operating a medical pump to overcome these deficiencies and accurately deliver a substance to a patient, such as an infant, in smaller increments for low flow rates in a more continuous manner (known as Low Flow Continuity). In general, Low Flow Continuity is defined as the ability of a pump to deliver at rates of 1 ml/hr to 0.1 ml/hr or less with periods of "no-flow" not exceeding 20 seconds and bolus volumes not exceeding 2 micro-liters. To meet the highest Emergency Care Research Institute (ECRI) industry standards for Low Flow Continuity and achieve an "Excellent" ECRI rating, the pump must at least deliver fluid in increments no greater than two micro-liters at a flow rate of 0.1 milliliter per hour with a maximum "no-flow" period of 20 seconds.

The present invention is provided to solve the problems discussed above and other problems, and to provide advantages and aspects not provided by prior medical pumps. A full discussion of the features and advantages of the present invention is deferred to the following detailed description, which proceeds with reference to the accompanying drawings.

SUMMARY OF THE INVENTION

The present invention is directed to a medical pump with an improved continuity low flow delivery system and method, for use with a pumping chamber, for example in a cassette, is disclosed. The pump includes a pump drive for exerting a force on the pumping chamber and a sensor for sensing the force/pressure exerted by the pump drive on the pumping chamber. A pump drive position sensor can also sense the position of the pump drive. The medical pump includes a processing unit and a memory having a programming code adapted to calculate the rate of change of the sensed force/pressure values and determine whether the rate of change of the sensed force/pressure values meets a rate of change threshold. Once the rate of change threshold is met, the programming code is adapted to calculate a remaining pump drive travel value, such as a linear distance, an angular distance, or a time, for determining how much farther the pump drive should travel before the end of an effective pump cycle.

The programming code is further adapted to trigger one or more signals to drive the pump drive for the remainder of the effective pump cycle using the remaining pump drive travel value.

In one embodiment, the pump drive of the medical pump includes a stepper motor. In an alternative embodiment, the pump drive includes a direct current motor. Either embodiment can be arranged to drive the motor in a constant speed arrangement or in a variable speed arrangement. The programming code is further adapted to calculate an estimated incremental delivery volume. The medical pump can also include a pumping element, and the pump drive drives the pumping element for exerting a force on the pumping chamber.

In a particular embodiment, the pump drive drives a cam which drives a plunger for exerting a force/pressure within a pumping chamber. In such an embodiment, the medical pump will operate in cycles, each of which is separated into three phases. The first phase is a pressurization phase wherein the pump drive drives a cam which causes the plunger to exert a force to the pumping chamber of the cassette until the outlet valve of the pumping chamber "cracks" and begins effective delivery of the substance. As will be explained in detail below, the medical pump prevents false detection of pump chamber "cracking" and makes particular determinations and calculations based on accurate detection of when effective delivery is actually occurring, so as to provide continuity at low flow delivery rates. In this embodiment, the second phase begins when effective delivery begins, and thereby the pump begins to release a bolus volume of the substance. The stepper motor then steps through a calculated number of delivery steps according to a calculated time for such step until effective delivery is complete for the cycle. Once effective delivery is completed, retraction phase begins, wherein the pump drive drives the cam to cause the plunger to retract from applying pressure on the pumping chamber. The pumping chamber then expands and draws more substance into the pumping chamber for the next cycle. When retraction is complete, the cycle is complete and the next cycle is ready to begin.

In one embodiment, the medical pump continuously detects the position of the pump drive and determines a cycle start position from this position information. The medical pump drives the pump drive at a drive rate which is based on a desired delivery rate, and senses a plurality of force/pressure values using the force/pressure sensor, which are representative of the force/pressure exerted on the force/pressure sensor as the driving of the pump drive occurs. The programming code is adapted to calculate the rate of change of the sensed force/pressure values, and determine in a first determination step whether the rate of change of the sensed force/pressure values meets a first rate of change value or threshold. If the first determination step is true, the programming code is further adapted to determine in a second determination step whether the rate of change of the sensed force/pressure values meets a second rate of change value or threshold. If the second determination step is true, the programming code is further adapted to calculate a remaining pump drive travel value for determining how much farther the pump drive should travel before the end of an effective pump cycle, and cause the pump to complete the effective pump cycle delivery using the remaining pump drive travel value.

In another embodiment, the medical pump calculates the remaining pump drive travel value by having effective cycle travel value information and determining an already traveled cycle value by using the continuous detection of the position of the pump drive and using this position information when the second determination step is true. The programming code is adapted to calculate the remaining pump drive travel value by subtracting the already traveled cycle value from the effective cycle travel value. When a stepper motor is used, once the remaining pump drive travel value is determined, a pump drive step value to complete the effective cycle can be determined by dividing the remaining pump drive travel value by a step travel size value.

In one embodiment, the first and second rate of change values are both predetermined values, such as a set amount of change in force per time. In addition, the first determination step can determine whether the rate of change of the sensed force/pressure values is greater than the first rate of change value, and the second determination step can determine whether the rate of change of the sensed force/pressure values is less than a second rate of change value. In various embodiments, the first rate of change value can be equal to, less than, or greater than the second rate of change value. In another embodiment, the first and second rate of change values can be calculated, such as for each cycle. One example of this calculation is using a predetermined percentage of a highest rate of change value from a previous cycle.

The medical pump can prevent the detection of false effective delivery occurring in various ways, as indicated above. The medical pump can also perform this function by determining whether the pump drive has traveled beyond a minimum allowable pump drive travel value for a cycle. A medical pump can also determine whether the pump drive has traveled beyond a maximum allowable pump drive travel value for a cycle. The medical pump can further calculate an average force/pressure value for each of a plurality of time intervals, and use the averaged force/pressure values to determine the rate of change of the sensed force/pressure values, instead of using directly sensed values to perform at least the threshold determination steps.

To prevent false detection of when effective delivery begins, the medical pump can additionally or alternatively determine whether a predetermined initial travel value, such as a linear distance, an angular distance, or a time, has been met in relation to the cycle start position such as a linear distance, an angular distance, or a time. Once this value has been met, the medical pump can prevent the above first determination step from occurring, prevent the above step of sensing the plurality of force/pressure values, and/or prevent the above step of calculating the rate of change of the sensed force/pressure values. Alternatively or in addition to the above prevention techniques, the medical pump can determine whether an additional travel value has been met after the above first determination step is true. If so, the medical pump can prevent the above second determination step from occurring, prevent the above step of sensing the plurality of force/pressure values, and/or prevent the above step of calculating the rate of change of the sensed force/pressure values.

As an example of one of the further effective delivery detection techniques, the medical pump determines a cycle start position, drives the pump drive at a drive rate which is based on a desired delivery rate, senses a plurality of force/pressure values over time using the force/pressure sensor, which are representative of the force/pressure exerted on the force/pressure sensor as the driving of the pump drive occurs, determines whether a predetermined initial travel value has been met in relation to the cycle start position, and calculates the rate of change of the sensed force/pressure values. However, the medical pump prevents sensing the plurality of force/pressure values and/or calculating the rate of change of the sensed force/pressure values until a predetermined initial travel value has been met. The medical pump determines whether the rate of change of the sensed force/pressure values is less than a threshold rate of change value, and if the rate of change of the sensed force/pressure values is less than the threshold rate of change value, the medical pump calculates a remaining pump drive travel value for determining how much farther the pump drive should travel before the end of an effective pump cycle. The medical pump then completes the effective pump cycle delivery using the remaining pump drive travel value.

In a further example, if the rate of change of the sensed force/pressure values has met the threshold rate of change value, then the medical pump determines whether a predetermined further travel value has been met, and drives the pump drive based on the predetermined further travel value. If the predetermined further travel value has been met and/or fulfilled, then the medical pump calculates a remaining pump drive travel value for determining how much farther the pump drive should travel before the end of an effective pump cycle. The medical pump then completes the effective pump cycle delivery using the remaining pump drive travel value.

In one particular embodiment, such as a syringe pump, the pump determines the delivery cycle start position and determines the amount, such as a weight or a volume, of a substance remaining to be delivered. The medical pump drives the pump drive at a drive rate which is based on a desired delivery rate, senses a plurality of force/pressure values over a travel distance using the force/pressure sensor, which are representative of the force/pressure exerted on the force/pressure sensor as the driving of the pump drive occurs, and determines the rate of change of the sensed force/pressure values over the travel distance. The medical pump also determines in a first determination step whether the rate of change of the sensed force/pressure values meets a first rate of change value, and if the first determination step is true, determines whether the amount of the substance remaining to be delivered has changed. If the amount of the substance remaining to be delivered has changed more than a change threshold, the medical pump completes the delivery cycle. If the amount of the substance remaining has not changed more than a change threshold, the medical pump considers that no effective delivery has occurred in one or more steps or movements, and considers that some form of "sticking" is taking place. In order to unstick one or more of the moving parts of the medical pump, the medical pump can drive the pump drive in a reverse direction for unsticking the substance delivery. Additional successive forward and then reverse movements of the pump drive can be performed, which can be referring to as "dithering," in order to unstick the delivery.

In one embodiment, the pumping chamber formed from a line, such as a tube segment, and a plurality of pumping elements, such as fingers, are provided for exerting a pressure/force on the line and the pumping chamber, such as within a peristaltic medical pump. The arrangement and process steps of the prior embodiments equally apply to this embodiment, which one of ordinary skill in the art would understand from review of the above embodiments, below description, and drawings.

One advantage of the present system and method is that the ECRI requirements for an "Excellent" rating are achieved. Specifically, the medical pump delivers a substance in increments or bolus volumes of no greater than two micro-liters at a flow rate of 0.1 milliliter per hour, with "no-flow" periods of less than 20 seconds f. Another advantage of the present invention is that each step of the delivery of the substance is consistent within a small error margin.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings.

DETAILED DESCRIPTION

Figure 1:
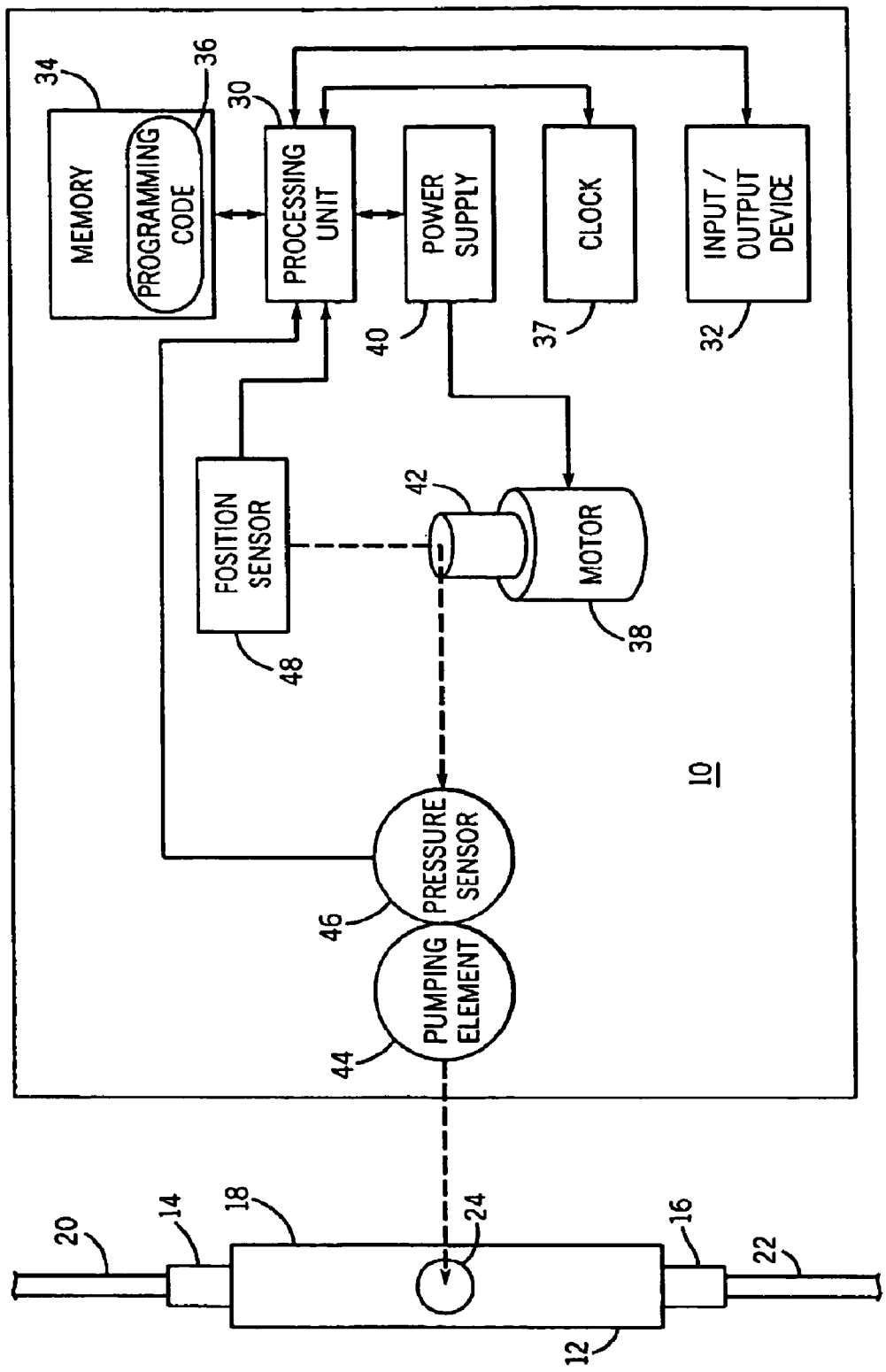
FIG. 1 is an illustration of one embodiment of the medical pump of the present invention.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the invention to the embodiments illustrated.

A medical pump includes but is not limited to enteral pumps, infusion pumps, cassette pumps, syringe pumps, peristaltic pumps, or any positive displacement fluid pumping device for the delivery of fluids intravenously or intra-arterially to a patient. Referring initially to FIG. 1, one embodiment of a medical pump 10 is provided in connection with a disposable pumping chamber, such as a cassette 12 or tube, for delivering a substance, such as a fluid, to a patient. In various embodiments of the medical pump of the present invention, the pumping chamber is a portion of at least one of a cassette, a tube, and/or a syringe, depending on the type of medical pump. The medical pump 10 provides a mechanism for adjusting an actual delivery of the substance based on variations from nominal data used to estimate pump performance. A processing unit 30 is included in pump 10 and performs various operations described in greater detail below. An input/output device 32 communicates with the processing unit 30 and allows the user to receive output from processing unit 30 and/or input information or commands into the processing unit 30. Those of ordinary skill in the art will appreciate that input/output device 32 may be provided as a separate display device and/or a separate input device. A memory 34 communicates with the processing unit 30 and stores code and data necessary for the processing unit 30 to calculate and output the operating conditions of pump 10. The memory 34 stores a programming code 36 formed in accordance with the present invention for processing data to determine and control the operating condition of the pump 10. A clock 37 is used to keep time in the pump 10. The clock 37 is connected to the processing unit 30, and provides the processing unit 30 with time information for correlating data over time or conducting time sensitive activities. An electric motor 38 is controlled by processing unit 30 and is energized by a power supply 40 to serve as a prime mover for rotatably driving a shaft 42 connected to the motor 38. The processing unit 30 orders the motor 38 to run at a constant speed or at different speeds, depending on the motor being used and depending on the flow rate desired through the pump 10. The down-stroke or delivery portion of the stroke has the motor 38 running directly from power supply 40. The up-stroke, retract or fill portion of the stroke is run at a voltage set by the processing unit 30, so that the retract times are varied by the processing unit 30, where higher desired flow rates require faster retract speeds. A pumping element 44, such as a plunger, is operatively associated with the shaft 42. When energized, the pumping element 44 reciprocates back and forth to periodically downstroke, causing pumping element 44 to press on pumping chamber 24, and expel fluid therefrom. On an up-stroke, pumping element 44 releases pressure from pumping chamber 24 and thereby draws fluid from inlet port 14 into pumping chamber 24. Thus, the pumping element 44 intermittently pressurizes the pumping chamber 24 during a pumping cycle. The power supply 40, the motor 38, and/or the pumping element 44 together, alone, or in some combination thereof, may be considered a pump drive for the purposes of the present specification. Other parts and/or elements may also make up the pump drive, as one of ordinary skill in the art would understand. In addition, parts of each of the power supply 40, the motor 38, the pumping element 44, and/or other elements can make up what is referred to herein as the pump drive, with the understanding that the pump drive is controlled by the processing unit 30 for driving the delivery of the substance to the patient through the use of the pumping chamber.

A force/pressure sensor 46 is operatively associated with the pumping element 44 to detect the force or pressure exerted by the pumping element 44 on the pumping chamber 24. As shown in FIG. 1, the sensor 46 can be directly connected to the pumping element and positioned in-line with the pumping element 44, between the pumping chamber 24 and the shaft 42 of the motor 38. In this embodiment, the sensor 46 is the only force/pressure sensor included in the medical pump 10, and operates to sense the force/pressure on pumping element 44 as well as to generate a force/pressure signal based on this force/pressure. The force/pressure sensor 46 is in electronic communication with the processing unit 30 to send the force/pressure signal to the processing unit 30 for use in determining operating conditions of pump 10. One of ordinary skill in the art will appreciate that the pressure sensor 46 may be a force transducer, strain gauge, or any other device that can operatively sense the pressure or related force brought to bear on the pumping chamber 24 by pumping element 44.

A position sensor 48 is operatively associated with the pumping element 44 to directly or indirectly detect the position of the pumping element 44. The position sensor 48 tracks each pumping cycle of pump 10 by detecting the position of the pumping element 44 at each position within each cycle. As shown, the position sensor 48 is associated with the shaft 42. The position sensor 48 generates a pump drive travel signal by detecting the rotational position of the shaft 42. The position sensor 48 is in electronic communication with the processing unit 30 to send the position signal to the processing unit 30. The processing unit 30 utilizes this information in various ways as will be described in greater detail below. One way includes associating the incoming force/pressure data with a particular travel value within the pumping cycle, such as a time, a linear distance, and/or rotational distance or angle of travel. One of ordinary skill in the art will appreciate that the position sensor 48 could alternatively track a cam attached to the shaft 42 or the pumping element 44. Additionally, one of ordinary skill in the art will appreciate that the position sensor 48 as used herein includes but is not limited to mechanical indicators, such as pivoting dial indicators, electronic switches, Hall Effect sensors, and optical based position detectors. The resolution of the position sensor 48 assists in achieving improved continuity, as will be better understood from the below description. In low friction pumping systems, finer pump drive step sizes and higher resolution pump drive position sensors 48 can be used. In one embodiment, the pump drive position sensor 48 has a resolution of about 0.35 mils for a 0.1 mL/hr. delivery rate. It has been determined that resolutions from at least about 0.15 mils can induce rates as low as 0.04 mL/hr. and still meet the "Excellent ECRI low flow continuity" rating. The step size is selected as a function of the desired delivery rate, and values anywhere between 0.15 and 0.45 mils will provide significant continuity improvements for rates between 0.04 and 1.0 mL/hr.

In a preferred embodiment, the motor 38 is a brush DC motor with a 128 count magneto-resistive encoder that is used in quadrature, for a total resolution of 512 counts per motor revolution. Depending on the number of motor shaft 42 rotations needed to perform a pump cycle, the cycle can be divided into a very fine number of positions. For example, if it takes 10 rotations of the pump shaft 42 to complete one pumping cycle or stroke (360 degrees in one embodiment), each cycle can be separated into 5120 travel positions or values. Thus, in this example, the position sensor 48 can provide information which allows for a resolution of 5120 travel positions per cycle for the processing unit 30 to determine and/or utilize within other calculations and determinations. One such motor is made by Portescap (a Danaher company), under model number 16G88.214E, MR128, B1627:1. The use of this or similar motors will be described in greater detail below.

Figure 2:
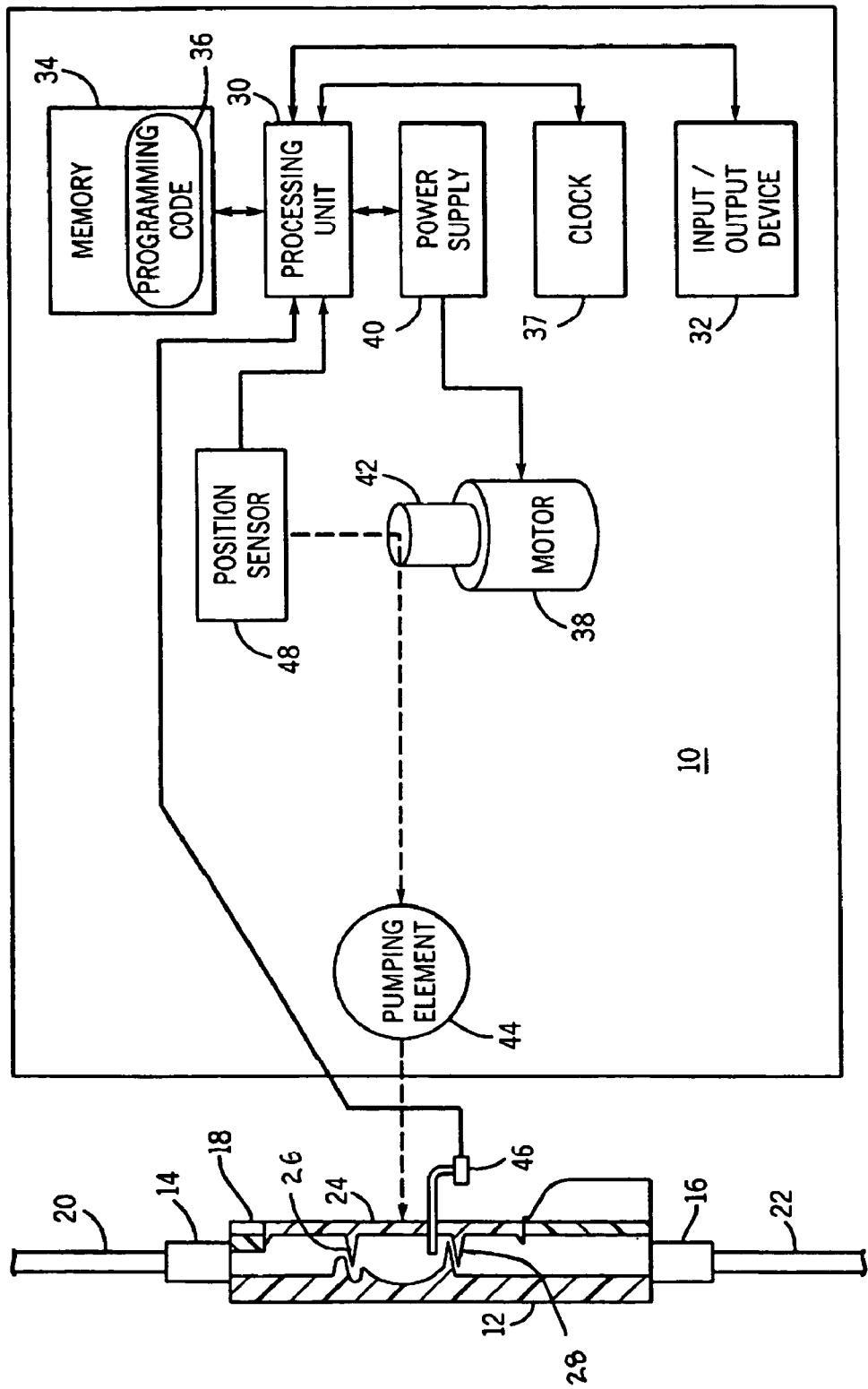
FIG. 2 is an illustration of another embodiment of the medical pump of the present invention.

Referring to FIG. 2, a similar arrangement is shown as FIG. 1. However, a specific cassette 12 is depicted with the internal construction of the cassette 12 shown. As also shown in FIG. 1, the cassette 12 may include an inlet 14 and an outlet 16 formed in main body 18. An inlet fluid line 20 couples the inlet port 14 on the main body 18 to a fluid source such as an IV bag or other fluid container. Similarly, an outlet fluid line 22 couples the outlet port 16 on main body 18 to the body of a patient. As shown in FIG. 2, an inlet valve 26 and outlet valve 28 are located within the main body 18. The pumping chamber 24 is connected in fluid flow communication between the inlet port 14 and the outlet port 16. The pumping chamber 24 operates to meter fluid through the cassette 12.

The inlet valve 26 resides between inlet port 14 and the pumping chamber 24. Inlet valve 26 operates to physically open and close the fluid communication between inlet port 14 and pumping chamber 24. The outlet valve 28 resides between the pumping chamber 24 and outlet port 16. Outlet valve 28 operates to physically open and close the fluid communication between pumping chamber 24 and outlet port 16. The pumping chamber 24, inlet valve 26, and outlet valve 28 are all operatively associated with the pump 10 to control the flow of fluid through the cassette 12. The cassette is a passive valve system requiring pressurization of the pumping chamber 24 prior to fluid delivery. Inlet valve 26 and outlet valve 28 react to the pressure of the pumping element 44 on the pumping chamber 24. In operation, a substance such as a fluid enters through the inlet 14 and is forced through outlet 16 under pressure. The fluid is delivered to the outlet 16 when the pump 10 displaces the membrane 23 and thereby compresses the pumping chamber 24 to expel the fluid. Additional details of this cassette and other details and information may be found in U.S. Patent Application Publication No. 2005/0214129 A1, published Sep. 29, 2005, the entirety of which is hereby incorporated by reference herein and made a part of this specification.

In the embodiment of FIG. 2, the force/pressure sensor 46 comprises a pressure probe located at least partially within the pumping chamber 24 of the cassette 12. The current signal from pressure probe is proportional to the force exerted on the pumping chamber 24 by the pumping element 44. As is also the case in FIG. 1, the force/pressure sensor 46 is the only force/pressure sensor included in the medical pump 10, and operates to sense the force/pressure on pumping element 44 as well as to generate a force/pressure signal to the processing unit 30 based on this force/pressure.

The medical pump 10 of the present invention provides a mechanism for controlling or adjusting an actual delivery of fluid based on variations from nominal data used to estimate pump performance. The processing unit 30 retrieves the operating condition programming code 36 from memory 34 and applies it to the force/pressure and travel data received during a pump cycle. The force/pressure data and travel data are processed by the processing unit 30. Sensing the force/pressure, for example that the pumping chamber 24 exerts against the pumping element 44, and analyzing that force/pressure data can determine various parameters for use in operating the medical pump 10. The processing unit 30 utilizes these parameters in a closed loop cycle/stroke feedback system to determine and/or calculate delivery parameters.

Figure 3:
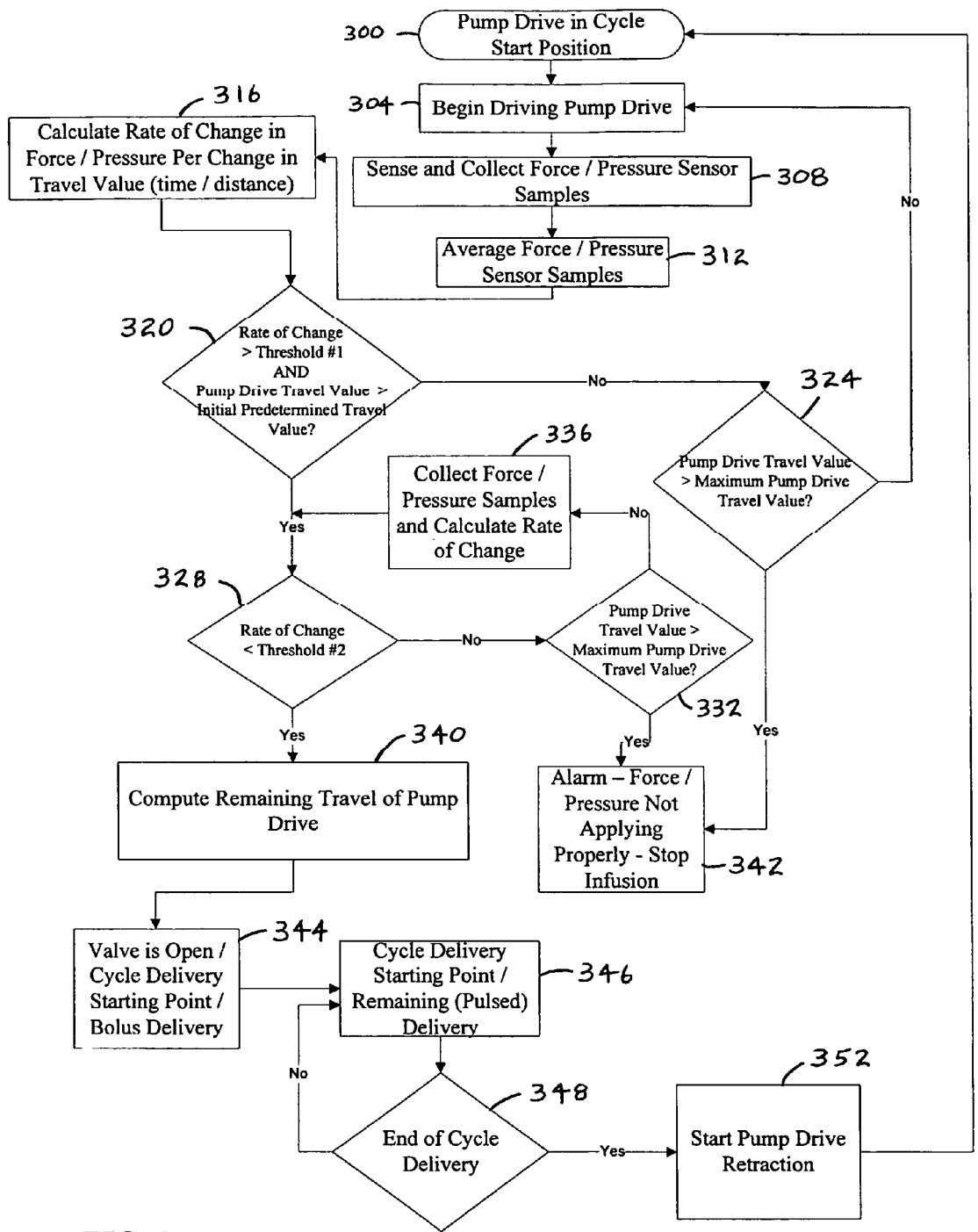
FIG. 3 is a flow chart of one method of operating one embodiment of the medical pump of the present invention.

Specifically, in one embodiment, such as the embodiment of FIG. 2, the processing unit 30 executes the programming code 36. Referring to FIG. 3, the execution of one embodiment of the programming code 36 is shown. Block 300 represents the pump drive, such as the motor 38 and/or the pumping element 44, in a cycle start position. Block 300 also represents the end of the previous pumping cycle. Block 304 represents a step of beginning driving the pump drive, to begin causing the pumping element 44 to advance toward and eventually apply a force/pressure on the pumping chamber 24. The cycle or pump drive start position has a pump drive position value and/or a time value associated therewith, which is stored in the memory 34 by the processing unit 30 at the start of the cycle. The cycle begins at 0 degrees, or Bottom Dead Center (BDC) in a "cam" embodiment, with the pumping element 44 applying a force/pressure to the pumping chamber 24 a minimal amount at this point. The start position of the pump drive, such as the pumping element 44, is at 0 degrees. This begins the pressurization phase of the cycle. Empirical data has shown that the true beginning and end of the pressurization phase ranges from about 0 degrees to about 30 degrees. However, determining the actual end of pressurization phase and the beginning of delivery phase, instead of false indications of this event, is significant in achieving one or more aspects of the present invention. During the pressurization phase of the cycle, the pumping element 44 moves into the cassette 12 (which may be referred to as the pressurization stroke because fluid is compressed in pumping chamber 24 of the cassette 12 in one embodiment) building force/pressure within the pumping chamber 24, while the outlet valve 28 remains closed.

While the driving of the pump drive continues through at least the pressurization phase, block 308 represents the sensor 46 continuously sensing the force/pressure and the processing unit 30 storing the sensed force/pressure samples in the memory 34. Block 312 represents that the processing unit 30 can calculate an average force/pressure value for each of a plurality of time intervals, store the averaged force/pressure values in the memory 34. The processing unit 30 can utilize these averaged force/pressure values within further calculations and determinations, as described herein. In particular, block 316 represents the processing unit 30 using the actual or averaged sensed force/pressure values from the sensor 46 stored in memory 34 to determine or calculate a rate of change of the sensed force/pressure values, over time or over a travel of the pump drive, such as a linear or angular travel distance or angle. The processing unit 30 stores these rate of change values in the memory 34.

With continued reference to FIG. 3, block 320 represents the processing unit 30 determining whether the determined or stored rate of change value of the sensed force/pressure values meets a rate of change value or threshold. In particular, before the processing unit 30 of the medical pump 10 determines whether a drop in sensed force/pressure values represents a significant event in determining whether the end of the pressurization phase is complete, the programming code 36 can require an initial value or first threshold for the rate of change before such a drop is deemed significant. This first threshold determination assists in preventing a false determination of the end of the pressurization phase. In one embodiment, the processing unit 30 determines whether the first rate of change threshold has been exceeded. Block 320 also represents the processing unit determining whether a predetermined initial travel value has been met in relation to the cycle start position. In particular, empirical data indicates that the end of the pressurization phase will not occur prior to at least the predetermined travel value, such as a travel time or a travel distance, being reached. In one embodiment, before the predetermined initial travel value has been met in relation to the cycle start position, the processing unit 30 will not perform at least one of the steps at block 308, block 316, block 320, and block 340, or other steps shown in FIG. 3, as appropriate to prevent a false determination of actual substance delivery beginning.

Thus, at block 320, the processing unit 30 determines if both the first rate of change threshold has been exceeded and a predetermined initial travel value has been exceeded. If both of these conditions are not met, block 324 represents the processing unit 30 determining whether the pump drive has actually traveled beyond a maximum allowable pump drive travel value, such as a maximum travel time or a maximum travel distance, for a cycle. In a preferred embodiment, the maximum allowable pump drive travel value is an angular distance of 50 degrees, which was empirically derived by testing a large sample of similar cassettes 12 for observed opening or "cracking" of the outlet valve 28. If the maximum threshold has been exceeded, then the processing unit 30 and programming code 36 will assume a medical pump operational problem has occurred and will proceed to block 342. Specifically, at block 342, the processing unit 30 and the programming code 36 will assume that the force/pressure being exerted on the pump drive, pumping element, and/or pumping chamber is not occurring properly and can trigger an alarm condition, and can cause the display of the medical pump 10 to show an alarm and/or issue an audible alarm. As represented at block 342, the processing unit 30 and programming code 36 can also be adapted to automatically stop the operation of the medical pump 10 and stop the pumping cycle under this alarm condition. Alternatively, the processing unit 30 and programming code 36 can be adapted to continue operating the medical pump 10 and continue the delivery cycle, but in a manner which may not meet or exceed the "Excellent" ECRI rating, although a lesser rating, such as a "Good" ECRI rating may still be achieved. Referring again to block 324, if this maximum threshold has not been met, then the processing unit 30 and programming code 36 will continue to cause driving of the pump drive, receive and store the sensed force/pressure values, calculate and store the rate of changes values, etc., as shown in FIG. 3 in blocks 328, 332, and 336.

If both the first rate of change threshold has been exceeded and the predetermined initial travel value has been exceeded, empirical data has been discovered to indicate that once the rate of change of the force/pressure values meets a second threshold, then a significant probability exists that the pressurization phase is complete and that actual delivery has begun. Specifically, at block 328, the processing unit 30 further determines whether the rate of change of the sensed force/pressure values meets a second rate of change value, and more specifically whether the rate of change of the sensed force/pressure values is less than a second threshold or rate of change value. If this determination is not met, then the flow proceeds to block 332 which represents the processing unit 30 determining whether the pump drive has actually traveled beyond a maximum allowable pump drive travel value, such as a maximum travel time or a maximum travel distance, for a cycle. If this maximum threshold has been exceeded, then the processing unit 30 and programming code 36 will again assume that the force/pressure being exerted on the pump drive, pumping element, and/or pumping chamber is not occurring properly and can trigger an alarm condition, and can cause the display of the medical pump 10 to show an alarm, issue an audible alarm, and/or take further action or non-action, as described above in relation to block 342. Referring again to block 332, if the maximum threshold has not been met, then the flow moves to block 336 which represents the processing unit 30 continuing to cause driving of the pump drive, receive and store the sensed force/pressure values, calculate and store the rate of changes values, etc., as shown in FIG. 3.

If the second rate of change threshold is met at block 328, or if the maximum pump drive travel value is exceeded at block 332 or block 324, then the programming code 36 and processing unit 30 proceeds to block(s) 340, which represent the processing unit 340 calculating a remaining pump drive travel value for determining how much farther the pump drive should travel before the end of an effective pump cycle. This is the point where the processing unit 30 and programming code 36 conclude that the pressure/force within the pumping chamber 24 is sufficient to open the outlet valve 28. During the delivery phase of the pumping cycle, the pumping element 44 moves into the cassette 12 so as to build incremental pressure within the pumping chamber 24 sufficient to reopen the outlet valve 28 and expel fluids from the pumping chamber 24 in a series of boli.

In one embodiment, the effective delivery cycle or delivery phase of the pump cycle is generally from about 30 degrees to 180 degrees of the rotation. However, since the processing unit 30 has accurately determined when the end of the pressurization phase has occurred and the processing unit 30 receives sensed position information of where the pump drive is positioned, such as the rotary or stepper motor position information, the processing unit 30 can determine how much additional travel is needed to complete the delivery phase of the pump cycle and utilizes this remaining travel value to accurately control the delivery phase to achieve low flow continuity and to meet or exceed an Excellent ECRI rating. In one embodiment, these determinations and calculations are performed as follows. For the purpose of the example, a desired delivery rate Q of 0.1 mL/hr. will be used, which is input by a caregiver or other means at the time of the programming of the pump for operation and stored in the memory 34. A stroke length calibration value $S_L$ (in.) of 0.0588015 will be used, which represents twice the cam offset in the case of a pump 10 driven by a DC motor 38 and cam arrangement, similar to that disclosed in U.S. Pat. No. 6,471,436. This value $S_L$ defines the full travel value of the pumping element 44 (in this case a plunger). A stroke volume calibration value $S_V$ (mL) of 0.0723 will be used, which is determined based on the stroke length from a lookup table, as one of ordinary skill in the art would understand. The calibration values are typically stored in a permanent memory 34 or otherwise hard coded into the medical pump 10 at the factory. An end of pressurization angle $E_P$ (degrees), where the end of the pressurization phase has been determined, is read by the processing unit 30 and is stored in the memory 34. This angle is a dynamic value, and is measured and determined for each pumping cycle. For the sake of the present example, the end of pressurization is 22.78645833 degrees. An end of stepping value $E_S$, or angle (degrees) in the present example, is also stored in a permanent memory 34 or otherwise hard coded into the medical pump 10 at the factory. In the present example, this angle is set at 175 degrees, as no significant or effective delivery of the substance or fluid is provided between the angles of 175 degrees and 180 degrees. Empirically, it has been determined that this angle is the end of when delivery occurs for a given stroke. Thus, in the present example, the remaining travel value is a distance and/or time between the angles of 22.78645833 degrees and 175 degrees. A pump drive or plunger step size $S_S$ (in.) is known based on the desired delivery rate Q. This parameter is determined and stored in the memory 34. Thus, for a delivery rate Q of 0.1 mL/hr., the step size for the pump drive is 0.00035 in. A pump drive step time $T_M$ (seconds), to move the pump drive from one step to the next step (or pulse) (0.00035 in. in this example) is determined and stored in the memory 34 as well. Thus, in this example the pump drive step time is 0.5 seconds. A pump drive retract time $T_R$ (sec.) is also stored in a permanent memory 34 or otherwise hard coded into the medical pump 10 at the factory. $T_R$ represents an estimated amount of time it takes for the pump drive to move from the end of the delivery phase of the present cycle to the beginning of the next cycle, or the amount of time it takes for the plunger to retract to the cycle start position in this example, which in this example is 2 seconds. A pump drive RPM value $P_M$ is also stored in a permanent memory 34 or otherwise hard coded into the medical pump 10 at the factory. In this example, a constant speed motor is used with a value of 25 RPM.

One additional significant parameter to utilize within the present example is the volume to be delivered due to pressurization, $V_P$ (mL). This value can also be preset at the factor in memory 34, as this assumed value is directly taken from the ECRI requirements for an "Excellent" rating. Specifically, the volume to be delivered due to pressurization is assumed to be 0.0020 mL. A lower value of $V_P$ could be selected for the algorithm if one wanted to exceed the requirements for an "Excellent" rating. Higher values of $V_P$ could be used to achieve ECRI "Good" or "Fair" ratings. With the above measured and determined information, additional delivery parameters can be determined and/or calculated, as follows:

$L_E$—Linear distance gap (in.) between end of effective delivery and half cycle (stroke), which is used as a correction factor (linear distance from 175 degrees and 180 degrees).

V—Volume delivered (mL) due to stepping (SUM of all $V_S$-$V_P$) (excludes pressurization bolus).

$T_P$—Pressurization duration time (sec.) (time from beginning of pump cycle to end of pressurization phase).

$L_P$—Linear travel (in.) due to pressurization phase (distance traveled over $T_P$).

$L_R$—Linear stepping range (in.) (pump drive (plunger) travel after end of pressurization ("cracking") until 175 degrees).

N—Number of steps processing unit 30 calculates to divide $L_R$ into to keep low flow.

$V_S$—Volume delivered (mL) per step (which is used a check if 2 uL per step is exceeded).

The processing unit 30 can determine a total step time $T_T$ for the pump drive to begin and complete the delivery phase. This is used to check if the 20 second requirement is exceeded. $T_T$ can be determined using the formula:

$$Q=(V_P+N \times V_S)/(T_P+(N \times T_T)+T_R)$$

A total dwell time $T_D$ can also be determined by the processing unit 30, for determining the overall time which effective delivery takes. The following provides additional information on the determination/calculation of the above parameters:

| | |
|---|---|
| $L_E$ (in) = | $0.5 \times S_L \times (1 - \cos((180 - E_S) \times \pi()/180))$ |
| V (mL) = | $S_V - V_P$ |
| $T_P$ (s) = | $E_P \times 60/((P_M/27) \times 360)$ |
| $L_P$ (in) = | $0.5 \times S_L \times (1 - \cos(E_P \times \pi()/180))$ |
| $L_R$ (in) = | $S_L - L_P - L_E$ |
| N = | $\text{ROUND}(L_R/S_S, 0)$ |
| $V_s$ (mL) = | $(S_V - V_P)/N$ |
| $T_T$ (s) = | $(3600 \times (V_P + N \times V_S)/Q - T_R - T_P)/N$ |
| $T_D$ (s) = | $[(3600 \times (V_P + N \times V_S)/Q - T_R - T_P)/N] - T_M$ |
| Q (mL/hr) = | $3600 \times (V_P + N \times V_S)/(T_P + (N \times T_T) + T_R)$ |

Thus, the values for these parameters using the above exemplary values are as follows:

| | |
|---|---|
| $L_E$ = | 0.00011 in. |
| V = | 0.07030 mL |
| $T_P$ = | 4.1015625 s. |
| $L_P$ = | 0.00229 in. |
| $L_R$ = | 0.05640 in. |
| N = | 161 |
| $V_S$ = | 0.00044 mL |
| $T_T$ = | 16.13 s. |
| $T_D$ = | 15.63 s. |

As mentioned above, one form of the motor 38 is a brush DC motor with a 128 count magneto-resistive encoder that is used in quadrature, for a total resolution of 512 counts per motor revolution. For this motor, one output shaft revolution translates into 27 motor revolutions due to gearbox reduction. Thus, when a pumping cycle or stroke is completed (i.e., one output shaft revolution is completed), the motor has turned 27 times. Thus, one stroke is equivalent to 512 times 27 counts or 13,824 counts. For each 38.4 counts, the output shaft will have turned 10 (13,824 counts/360°), or the output shaft turns 0.026° for every encoder count.

Thus, one step movement is a very fine travel distance. However, a smaller step size does not always translate into significant pumping element movement or delivery. For example, assuming at time $t_1$, the plunger is at 890, the plunger linear position will be $L_{cam}(1-\cos(89°))$ or 0.029476427". At time $t_2$, the motor is now at 89.026°, so the linear position is now $L_{cam}(1-\cos(89.0260))$ or 0.029490039". Therefore, the plunger has traveled 0.000013611 inches from 89° to 89.026°, clearly an insignificant distance. Further, friction in the plunger/cassette subsystem may prevent any movement at all. Thus, without any actual movement, there will be no effective delivery.

The present invention exceeds the "Excellent" ERCI rating of low flow continuity at 0.1 mL/hr., and likely even lower, at about 0.08 mL/hr. If the step size is lowered as well (currently it is set at 0.35 mil at 0.1 mL/hr). The limiting factor is not the pump drive encoder, but the friction that the medical pump system must overcome when stepping at a very fine rate. The step size should be large enough to overcome the medical pump system friction and the outlet valve cracking pressure.

Referring again to FIG. 3, block 340 represents the processing unit 30 performing one of more of the above exemplary determinations and/or calculations in order to calculate a remaining travel of the pump drive to complete effective delivery for the cycle. Once the processing unit 30 has made the necessary delivery parameter determinations, the processing unit 30 controls the driving of the pump drive, or stepping of the pump motor 38 in the present example, utilizing determined parameters such as the number of steps N to be used for the effective delivery of the delivery phase of the pump cycle and the size of each step $S_S$. Thus, block 344 represent the processing unit 30 sending a signal to stop the pump drive from continuously driving the pump drive since the pressurization phase is complete, at which point an initial bolus delivery occurs. The effective delivery then moves to block 346, which represents the processing unit 30 and programming code 36 sending one or more signals to the pump drive to drive the pump drive according to the calculated parameters in a pulsed delivery scheme.

Block 348 represents the processing unit 30 and programming code 36 continuing to determine whether the effective delivery cycle is complete. If the effective delivery cycle is complete, then the processing unit 30 causes the pump drive to be reset to the beginning of the next cycle. For example, in the present embodiment using the described cam, the pump drive is driven for the time $T_R$ to bring the pump drive to the beginning of the next cycle. In particular, the effective delivery phase of the pump cycle ends at 5 degrees short Top Dead Center (TDC), or 175 degrees of rotation, and a retraction or depressurization phase begins at 180 degrees, as shown in block 352. The depressurization phase depressurizes the pumping chamber 24, which occurs from about 180 to 210 degrees. During the depressurization phase, the pumping element 44 moves out of the cassette 12 (which is called the up-stroke, depressurization or inlet stroke) and the force/pressure drops off. As the pumping element returns to its initial position, while the inlet valve 26 remains closed, negative pressure builds within the pumping chamber 24. A refill phase within the retraction phase begins when the negative pressure within the pumping chamber 24 is sufficient to the open the inlet valve 26. During the refill phase, the pumping element 44 moves out of the cassette 12 building negative pressure within the pumping chamber 24 sufficient to open the inlet valve 26 and draw fluids into the pumping chamber 24. The refill phase of the retraction phase occurs from about 210 to 360 degrees, or Bottom Dead Center (BDC), which brings the pump drive to the beginning of the next cycle, as shown in block 300.

The pump drive step value can be a time to drive the pump drive a linear distance to drive the pump drive, an angular distance or degree for the pump drive to travel, and/or some other travel value. The motor can be driven at a constant rate or a variable rate, as will be described in greater detail below. In the above example, a constant rate motor or motor drive was used, which creates variable speed movement of the pumping element 44, such as a plunger. However, a variable speed motor or motor drive may be used to create constant speed pumping element movement, such as a constant speed plunger. The calculations, determinations and delivery scheme will change accordingly, as one of ordinary skill in the art would understand from the present description. Specifically, the following applies in an embodiment which implements a motor that drives a camshaft, with the rotating cam driving the plunger in a linear motion. This drive technique results in the plungers' linear velocity varying in a sinusoidal fashion when the motor rotational velocity is constant. This further leads to at least two possible implementations for achieving the ECRI "Excellent" rating for fluid delivery using a cam. One is to drive the plunger in a constant linear velocity and the other is to drive the motor in a constant rotational velocity or rotations per minute (RPM). For constant plunger velocity, the motor drives the plunger via a rotating cam. The constant plunger velocity pressurization scheme varies the motor RPM to keep the plunger velocity constant. Once pressurization is achieved, the remainder of the delivery stroke is divided into the required number of constant plunger displacement segments to achieve dwell times between plunger movements less than 20 seconds and bolus sizes less than 2 uL to comply with the ECRI "Excellent" rating. The constant RPM pressurization scheme allows the plunger velocity to vary. Once pressurization is achieved, the remainder of the delivery stroke is divided into the required number of constant motor angular movements such that no individual bolus will exceed 2 uL and the dwell times between bolus deliveries will be less than 20 seconds. Alternatively, a linear pump drive may be used to directly drive the pumping element 44 at a constant rate, and again, the calculations, determinations and delivery scheme will change accordingly. Other arrangements are possible, as one of ordinary skill in the art would understand and as described with reference to at least FIGS. 9 and 14 herein.

Figure 4:
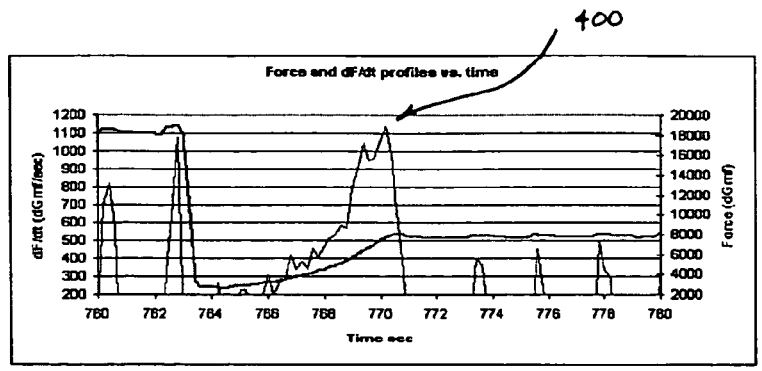
FIG. 4 is a graph of the sensed force/pressure values over time as well as the change in sensed force/pressure values over time for one embodiment of the medical pump of the present invention.
Figure 5:
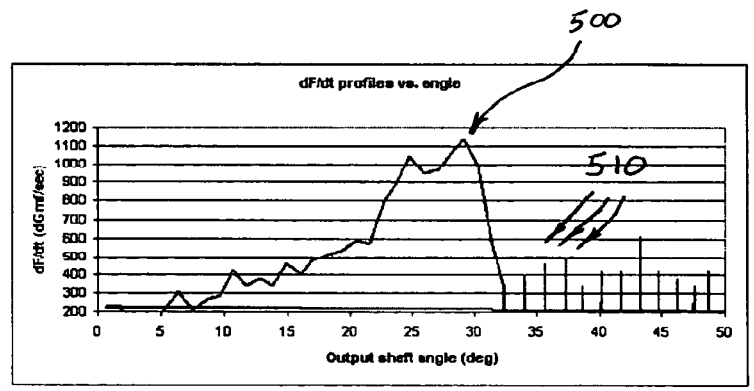
FIG. 5 is a graph of the change in the sensed force/pressure values over a pump drive travel angle for one embodiment of the medical pump of the present invention.

Referring to FIGS. 4 and 5, graphs of the sensed force/pressure values over time and over pump drive travel angle, as well as the change in sensed force/pressure values over time an over pump drive travel angle are shown for one embodiment of the medical pump 10. Mechanical and other friction can cause the first rate of change threshold to be met, which may otherwise cause a false determination of the end of the pressurization phase. For example, friction between the pumping element (plunger tip) and a cassette in the embodiments of FIGS. 1 and 2 can cause the first rate of change threshold to be met instead of actual force/pressurization due to pump drive travel. False triggering of the first threshold can induce long periods of no flow, which could violate the maximum 20 seconds as set by ECRI. In one embodiment of the medical pump 10, the first and second rate of change thresholds can be predetermined and stored in a permanent memory 34 or otherwise hard coded into the medical pump 10 at the factory. In one embodiment, the first and second rate of change thresholds can be set at 400 dGmf/sec dF/dt and 500 dGmf/sec dF/dt, respectively. As time and angle of movement increase within the graphs of FIGS. 4 and 5, the rate of change increases, surpasses the 400 dGmf/sec dF/dt value and then surpasses the 500 dGmf/sec dF/dt value. The rate of change value then peaks at a peak point 400, 500. Once the peak point is reached, the rate of change value then drops below the second threshold, 500 dGmf/sec dF/dt, indicating that the pressurization phase in complete and that the delivery phase is beginning. Thereafter, the pump drive provides pulsatile delivery, as shown through the pulses 510 in FIG. 5. Thus, FIGS. 4 and 5 show proper detection of the end of the pressurization phase and the beginning of the delivery phase, so that the proper determinations and calculations can be performed by the processing unit 30 for the delivery phase of the cycle.

Figure 6:
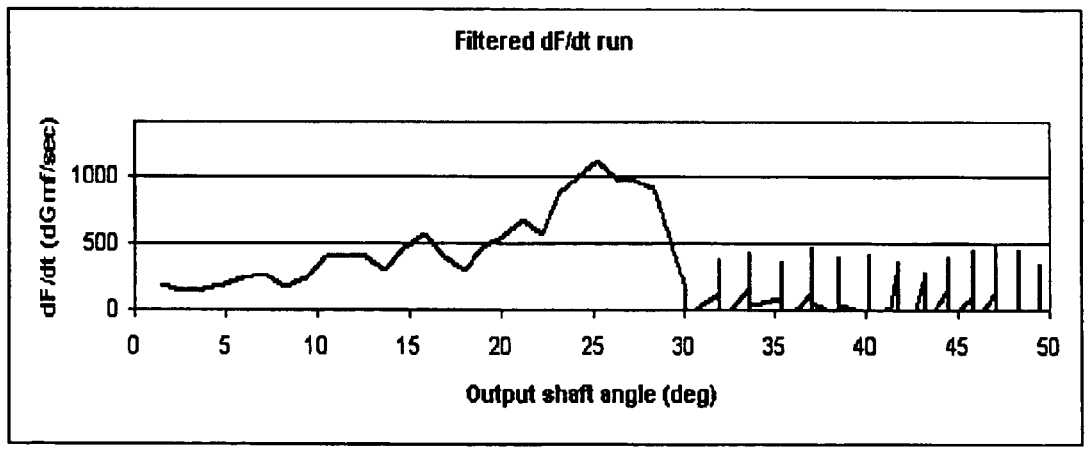
FIG. 6 is a graph of the change in the sensed force/pressure values over a pump drive travel angle for one embodiment of the medical pump of the present invention, after a filtering step is performed.

FIG. 6 is a graph of the change in the sensed force/pressure values over a pump drive travel angle for one embodiment of the medical pump after one or more filtering steps are performed. As mentioned, friction can induce high random dF/dt peaks, and can fool the system into believing that one of those peaks is actually a correct pressurization peak. When the medical pump 10 begins "stepping" within the pulsatile mode after a "false" end of pressurization determination, no fluid is actually delivered since the cassette 12 actually never pressurized correctly. As mentioned, this can induce long periods of no flow and no bolus. Rather than using lubricant or other inefficient preventative maintenance measures on the medical pump 10, or using other costly friction prevention design implementations, a programming code 36 filter can be used to cause the medical pump 10 to, in one embodiment, ignore any sudden increase above the first and second rate of change thresholds and any drop below the second rate of change threshold thereafter, if a certain amount of angular displacement has not been met. Specifically, the programming code 36 can be programmed to determine if a predetermined initial travel value has been reached, such as 10 degrees of angular travel, and prevent the processing unit 30 from performing certain steps prior to the predetermined initial travel value being met or exceeded. The steps which can be prevented from taking place include but are not limited to one or more of: sensing the plurality of force/pressure values; calculating the rate of change of the sensed force/pressure values; determining whether the rate of change of the sensed force/pressure values meet a threshold rate of change value; and/or calculating the remaining pump drive travel value, as understood from the above description.

After the initial predetermined travel value is reached, the processing unit 30 determines whether the first rate of change threshold has been met. If the first rate of change value has been met, the programming code 36 can also be programmed to drive the pump drive for the predetermined further travel value, such as an additional 6 degrees of angular travel. The processing unit 30 can also be programmed to continuously determine whether the predetermined further travel value has been met. Until the pump drive completes the predetermined further travel value, the processing unit 30 can be prevented from performing certain steps. These steps can include but are not limited to one or more of: sensing the plurality of force/pressure values; calculating the rate of change of the sensed force/pressure values; determining whether the rate of change of the sensed force/pressure values meet a threshold rate of change value; and/or calculating the remaining pump drive travel value, as understood from the above description. A predetermined initial travel value of about 6 degrees has shown to prevent false indications of the end of the pressurization phase. This value has also empirically shown not to be too large. A value which is too large may cause the end of the pressurization phase to be missed, or not be detected by the processing unit 30. FIG. 6 shows proper detection of the actual end of the pressurization phase and the beginning of the effective delivery phase using these filters.

Figure 7:
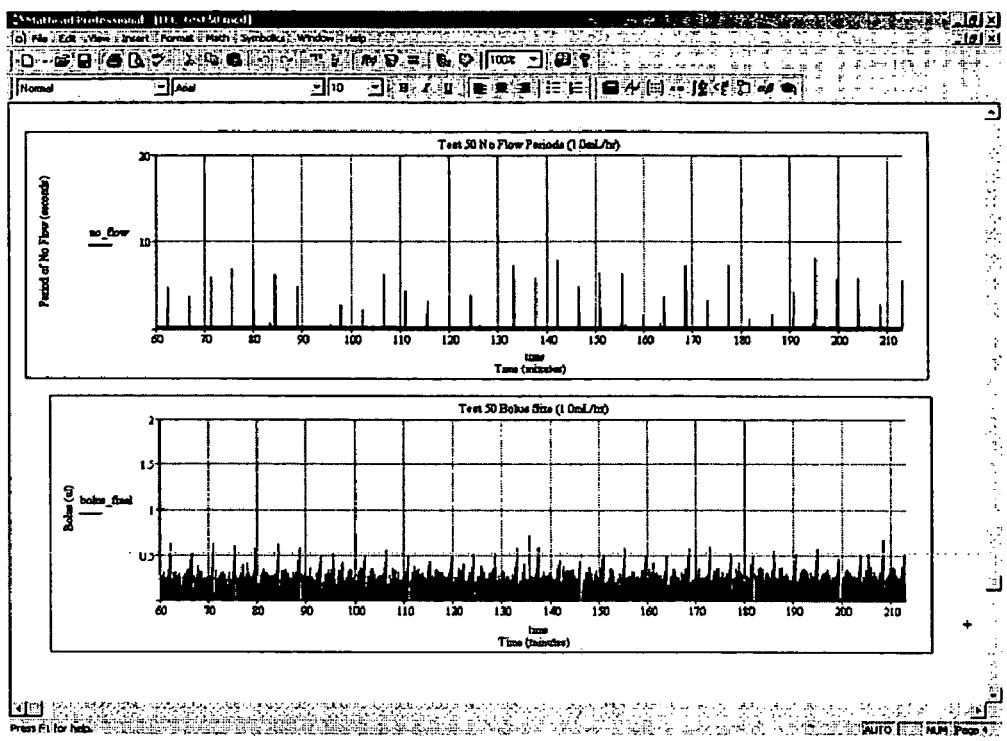
FIG. 7 is a concurrent graph of no flow delivery performance and bolus delivery performance of the embodiment of FIG. 2 at a first low flow delivery rate.
Figure 8:
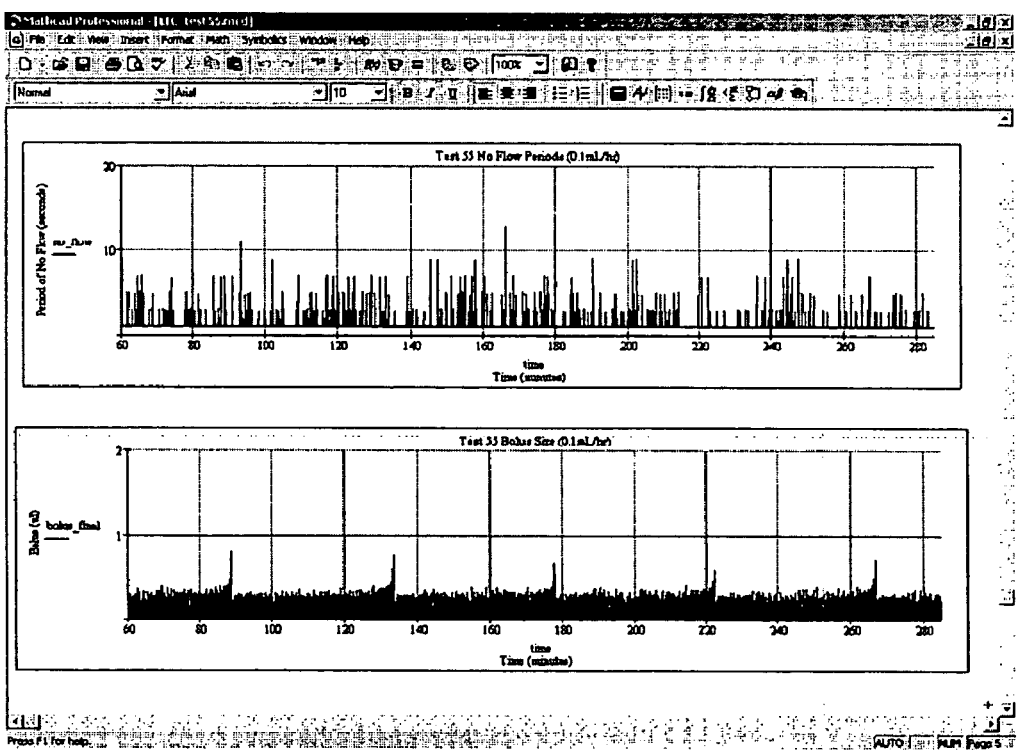
FIG. 8 is a concurrent graph of no flow delivery performance and bolus delivery performance of the embodiment of FIG. 2 at a second low flow delivery rate.

Referring to FIGS. 7 and 8, screen displays show dual graphs of no flow delivery performance and bolus delivery performance of the embodiment of FIG. 2 at a first low flow delivery rate and a second low flow delivery rate. Specifically, these graphs show LFC performance of the medical pump 10 at 0.1 mL/hr and 1.0 mL/hr., respectively. As indicated above, LFC is achieved through a pressurization phase followed by a pulsatile mode of delivery. The performance of the medical pump 10 shown with a top graph of FIGS. 6 and 7 depicting "no flow periods" results versus infusion time. No flow periods are time periods where no change or substantially no change in delivered volume is registered. To meet ECRI "Excellent" LFC rating in terms of no flow periods, those periods cannot exceed 20 seconds at 0.1 mL/hr. The tested medical pump 10 meets that requirement. As shown in FIG. 8, at 1.0 mL/hr, the pulsatile no flow periods are smaller than the pressurization no flow periods. The bottom graph of FIGS. 7 and 8 refers to "bolus size" results versus infusion time. Bolus sizes are reported in microliter and show the amount of fluid delivered within a fixed time period. To meet ECRI "Excellent" LFC rating in terms of bolus delivered, those volumes cannot exceed 2.0 uL at 0.1 mL/hr. The medical pump 10 tested also meets that requirement. At 0.1 mL/hr, the pulsatile boli are smaller than the pressurization boli in view of the programming code 36 design.

Figure 9:
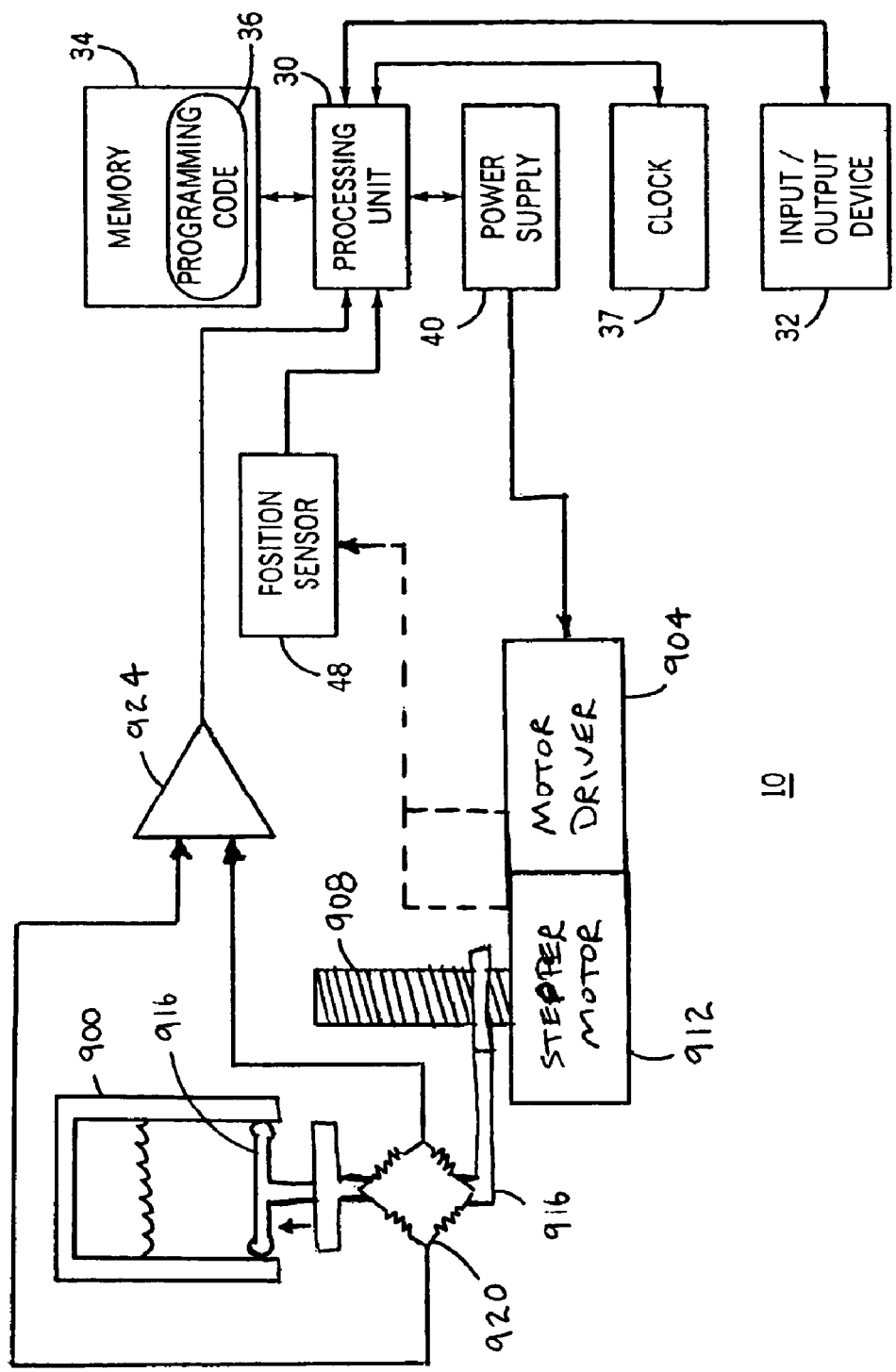
FIG. 9 is an illustration of another embodiment of the medical pump of the present invention.

FIG. 9 shows an additional embodiment of the present invention, which is similar to and utilizes similar functionality from embodiments described above. In one form of the medical pump 10 of FIG. 9, the medical pump 10 is a syringe pump. The medical pump 10 is provided in connection with a disposable substance or pumping chamber, such as a vial or syringe 900 for delivering a substance, such as a fluid, to a patient. A pump or motor drive 904 is controlled by processing unit 30 and is energized by a power supply 40 to serve as a prime mover for rotatably driving a threaded shaft 908 connected to the motor 912. The processing unit 30 orders the motor 912 to run at a constant speed or different speeds depending on the type of motor being used, and depending on the flow rate desired through the pump 10. A pumping element 916, is operatively associated with the shaft 908. When energized, the stepper motor 912 rotates the threaded shaft 908, which causes the pumping element 916 to move toward the pumping chamber 900, causing the pumping element 916 to press against the substance in the pumping chamber 900, and expel fluid therefrom. The power supply 40, the motor drive 904, the motor 912, and/or the pumping element 916 together, alone, or in some combination thereof, may be considered a pump drive for the purposes of the present specification. Other parts and/or elements may also make up the pump drive, as one of ordinary skill in the art would understand. In addition, parts of each of the power supply 40, the motor drive 904, the motor 912, the pumping element 916, and/or other elements can make up what is referred to herein as the pump drive, with the understanding that the pump drive is controlled by the processing unit 30 for driving the delivery of the substance to the patient through the use of the pumping chamber 900.

A force/pressure sensor 920 is operatively associated with the pumping element 916 to detect the force or pressure exerted by the pumping element 916 on the substance within the pumping chamber 900. As shown in FIG. 9, the sensor 920 can be directly connected to the pumping element 916 and positioned in-line with the pumping element 916, between the pumping chamber 900 and the threaded shaft 908 of the motor 912. In this embodiment, the sensor 920 is the only force/pressure sensor included in the medical pump 10, and operates to sense the force/pressure on pumping element 916 as well as to generate a force/pressure signal based on this force/pressure. The force/pressure sensor 920 is in electronic communication with the processing unit 30 through an amplifier 924 to send the force/pressure signal to the processing unit 30 for use in determining operating conditions of pump 10. One of ordinary skill in the art will appreciate that the pressure sensor 920 may be a force transducer or any other device that can operatively sense the pressure or related force brought to bear on the pumping chamber 900 by pumping element 916.

A position sensor 48 is operatively associated with the motor 912 and/or motor drive 904 to directly or indirectly detect the position of the pumping element 916. The position sensor 48 tracks the delivery of the substance from the pump 10 by detecting the position of the pumping element 916 at each position within the delivery. As shown, the position sensor 48 can be associated with the motor 912 and threaded shaft 908. The position sensor 48 generates a pump drive travel signal by detecting the rotational position of the threaded shaft 908. The position sensor 48 is in electronic communication with the processing unit 30 to send the position signal to the processing unit 30. The processing unit 30 utilizes this information in similar ways as described above, such as by associating the incoming force/pressure data with a particular travel value within the delivery, such as a time, a linear distance, and/or rotational distance or angle of travel. Additionally, one of ordinary skill in the art will appreciate that the position sensor 48 as used herein includes but is not limited to mechanical indicators such as pivoting dial indicators, electronic switches, Hall Effect sensors, and optical based position detectors.

The medical pump 10 of the present invention provides a mechanism for controlling or adjusting the delivery of fluid based on variations from nominal data used to estimate pump performance. The processing unit 30 retrieves the operating condition programming code 36 from memory 34 and applies it to the force/pressure and travel data received during a delivery. The force/pressure data and travel data are processed by the processing unit 30. Sensing the force/pressure, for example that the pumping chamber 900 exerts against the pumping element 916, and analyzing that force/pressure data can determine various parameters for use in the operating the medical pump. The processing unit 30 utilizes these parameters in a closed loop cycle/stroke feedback system to determine and/or calculate delivery parameters.

Figure 10:
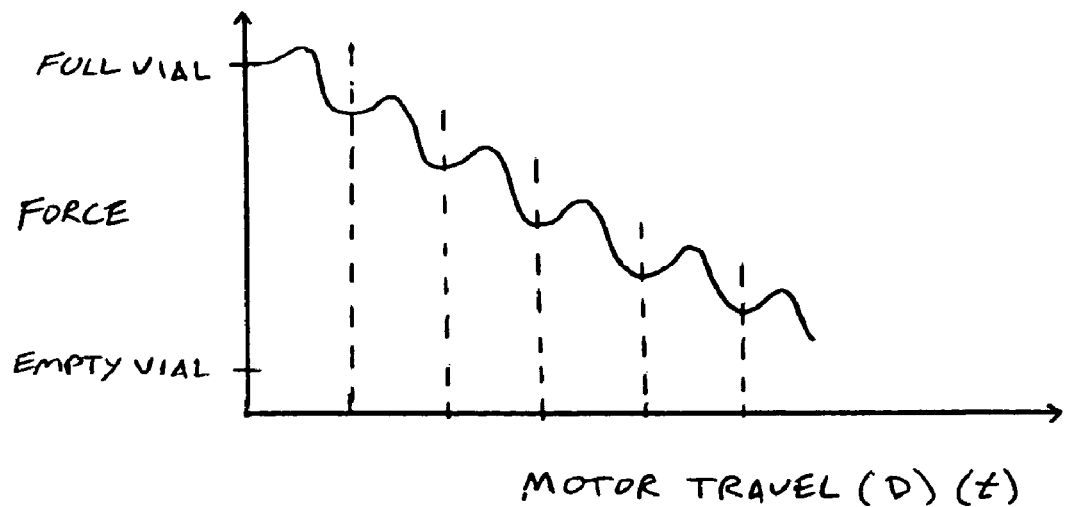
FIG. 10 is a graph of the sensed applied force/pressure over pump motor drive travel for the embodiment of FIG. 9, depicting normal operation.
Figure 11:
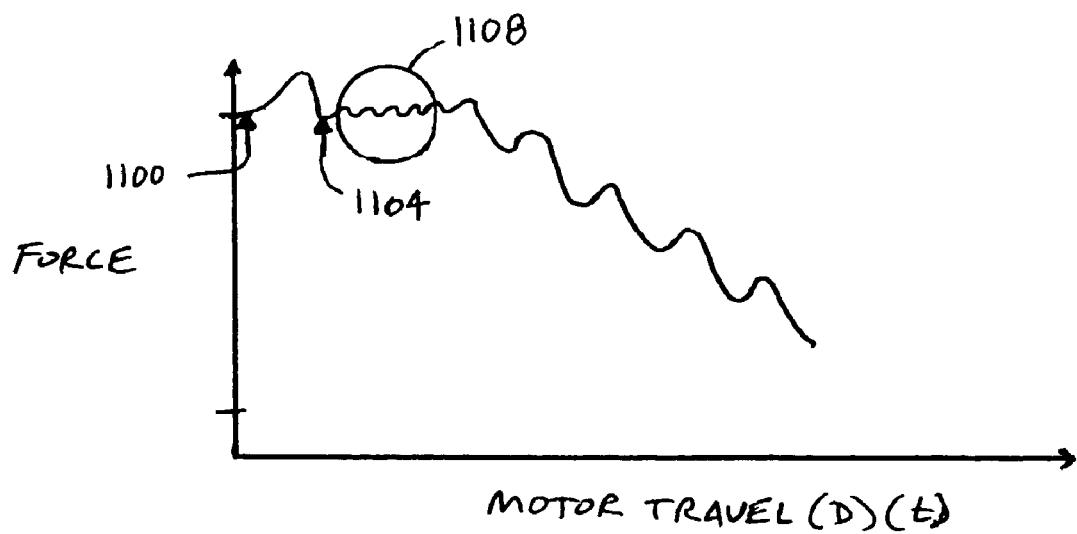
FIG. 11 is a graph of the sensed applied force/pressure over pump motor drive travel for the embodiment of FIG. 9, depicting an unsticking operation.

In the embodiment of FIG. 9, the processing unit 30 determines the delivery cycle start position and determines the amount, such as a weight or a volume, of a substance remaining to be delivered. A cycle for the purpose of this embodiment can be considered as the delivery of the substance to the patient or a time interval or over a pump drive or motor travel distance. A cycle can alternatively be considered as the entire delivery of the substance in the pumping chamber 900 to the patient. No pressurization phase and no retraction phase will be encountered without a cassette or cam being used. As the substance, such as a fluid, is delivered to the patient from the pumping chamber 900, the weight of the substance within the pumping chamber 900 decreases. Referring additionally to FIG. 10, a graph shows a sensed force/pressure values verses pump drive or pump travel in either time or distance. Various intervals are shown within the delivery, as separated by the dotted lines in this figure. A weight and/or a volume of the substance is measured and/or determined by the processing unit 30 at the beginning of each interval. Referring further to FIG. 11, a graph shows a sensed force/pressure values verses pump drive or pump travel in either time or distance. A second weight and/or a volume of the substance is measured and/or determined by the processing unit 30 for each interval. The medical pump 10 drives the pump drive at a drive rate which is based on a desired delivery rate and senses a plurality of force/pressure values over a travel distance using the force/pressure sensor 920, which are representative of the force/pressure exerted on the force/pressure sensor 920 as the driving of the pump drive occurs. The processing unit 30 further determines the rate of change of the sensed force/pressure values over the travel distance, and determines in a first determination step whether the rate of change of the sensed force/pressure values meets a first rate of change value. Similar to previous embodiments, the processing unit 30 is trying to determine if delivery for an interval has begun. If delivery for an interval has begun, then, the processing unit 30 determines whether the amount of the substance remaining to be delivered has changed. In one form of the present embodiment, the weight or volume of the substance in the pumping chamber will change if actual delivery is occurring. Thus, if the amount of the substance remaining to be delivered has changed more than a change threshold, then it is likely that any friction caused by the medical pump has not caused "sticking," and that actual delivery is occurring. If the amount of the substance remaining has not changed more than a change threshold, the processing unit 30 determines that no effective delivery has occurred in one or more steps or movements, and determines that some form of "sticking" is taking place. Specifically, FIG. 11 shows a first point 1100 where a weight or volume of the substance determination takes place in the processing unit 30 at the beginning of an interval, as the pump drive attempts to deliver the substance to the patient in a LFC. FIG. 11 also shows a second point 1100 where a weight or volume of the substance determination takes place in the processing unit 30 in the middle or toward the end of an interval, as the pump drive attempts to deliver the substance to the patient in a LFC. If the difference between the weight and/or volume values taken at the first point 1100 and taken at the second point 1104 does not meet a predetermined threshold value or does not change, then the processing unit 30 will determine that no effective delivery has taken place, and that the pump drive or other operating portion of the medical pump 10 is stuck. In order to unstick one or more of the moving parts of the medical pump 10, the processing unit 30 drives the pump drive in a reverse direction for unsticking the substance delivery. Additional successive forward and then reverse movements of the pump drive can be performed, which can be referred to as "dithering," in order to unstick the delivery, as is shown in circle 1108 in FIG. 11.

Figure 12:
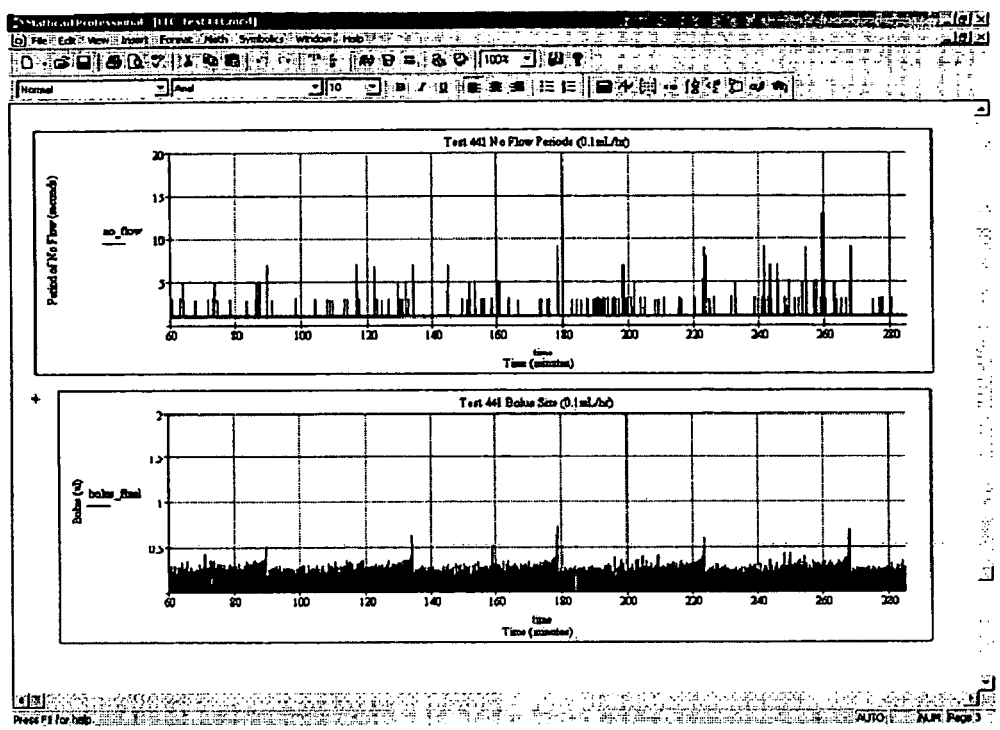
FIG. 12 is a concurrent graph of no flow delivery performance and bolus delivery performance of the embodiment of FIG. 9 at a first low flow delivery rate.
Figure 13:
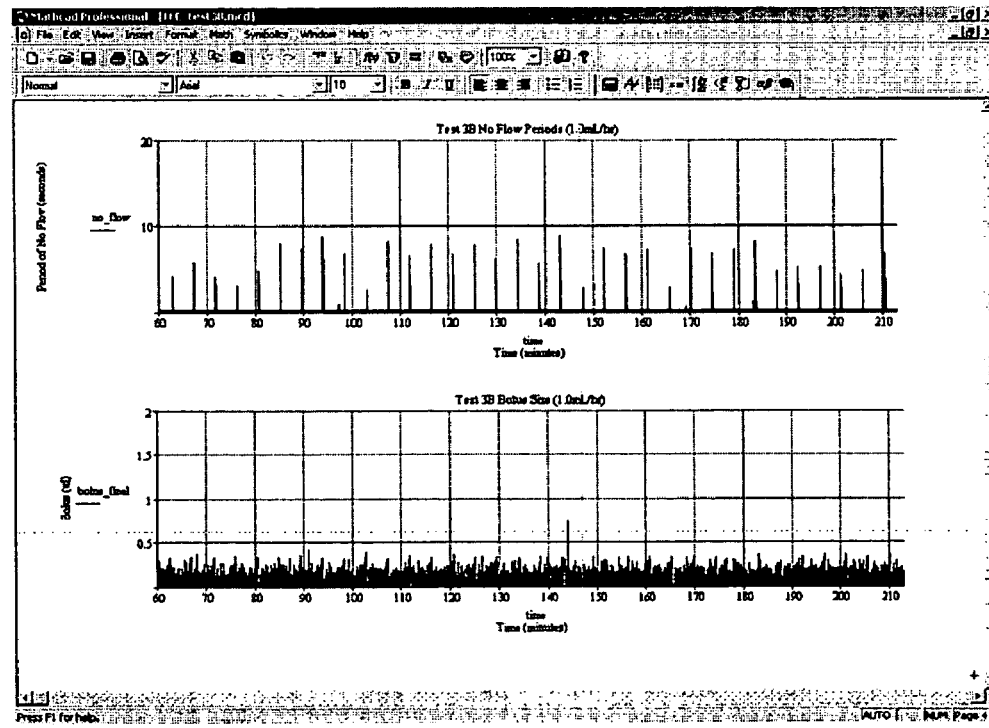
FIG. 13 is a concurrent graph of no flow delivery performance and bolus delivery performance of the embodiment of FIG. 9 at a second low flow delivery rate.

Referring to FIGS. 12 and 13, screen displays show dual graphs of no flow delivery performance and bolus delivery performance of the embodiment of FIG. 9 at a first low flow delivery rate and a second low flow delivery rate. Specifically, these graphs show LFC performance of the medical pump 10 at 0.1 mL/hr and 1.0 mL/hr., respectively. LFC is achieved through a pulsatile mode of delivery. The performance of the medical pump 10 is shown within a top graph of FIGS. 12 and 13 depicting "no flow periods" results versus infusion time. No flow periods are time periods where no change or substantially no change in delivered volume is registered. To meet ECRI "Excellent" LFC rating in terms of no flow periods, those periods cannot exceed 20 seconds at 0.1 mL/hr. As shown in FIG. 13, at 1.0 mL/hr, the pulsatile no flow periods are smaller than the pressurization no flow periods. The bottom graph of FIGS. 12 and 13 refers to "bolus size" results versus infusion time. Bolus sizes are reported in microliter and show the amount of fluid delivered within a fixed time period. To meet ECRI "Excellent" LFC rating in terms of bolus delivered, those volumes cannot exceed 2.0 uL at 0.1 mL/hr. The medical pump 10 tested also meets that requirement. At 0.1 mL/hr, the pulsatile boli are smaller than the pressurization boli in view of the programming code 36 design.

Figure 14:
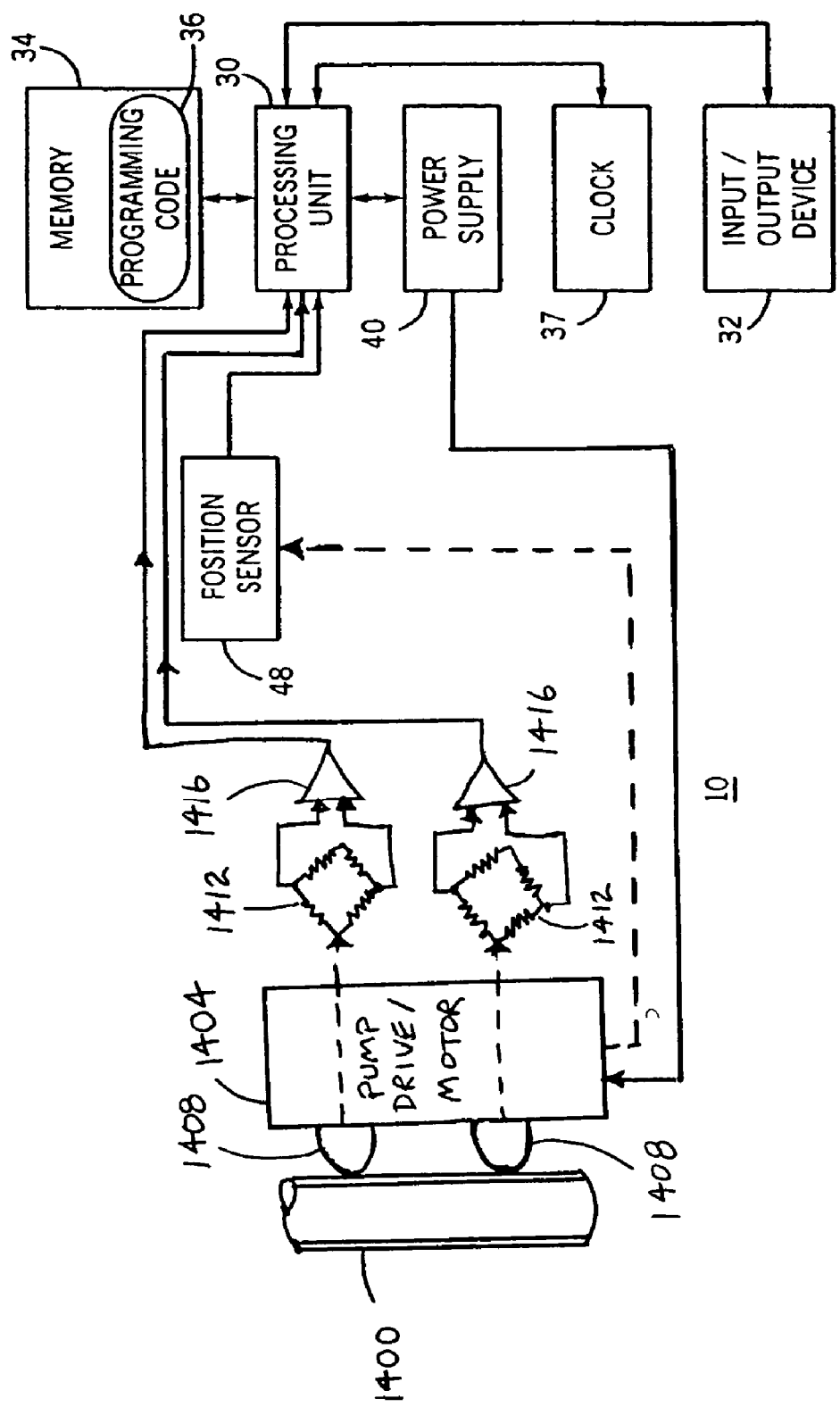
FIG. 14 is an illustration of further embodiment of the medical pump of the present invention.

FIG. 14 shows an additional embodiment of the present invention, which is similar to and utilizes similar functionality from embodiments described above. In one form of the medical pump 10 of FIG. 14, the medical pump 10 is a peristaltic pump. The medical pump 10 is provided in connection with a disposable substance or pumping chamber, such as a tube 1400 for delivering a substance, such as a fluid, to a patient. The medical pump 10 provides a mechanism for adjusting an actual delivery of the substance based on variations from nominal data used to estimate pump performance. A pump drive and motor, or set of motors 1404, is controlled by processing unit 30 and is energized by a power supply 40 to serve as a prime mover for linearly or rotatably driving one or more pumping elements or fingers 1408 connected to the pump drive/motor 1404. The processing unit 30 orders the pump drive/motor 1404 to run at a constant speed or at different speeds, depending on the motor being used and depending on the flow rate desired through the pump 10. The delivery portion of the cycle or stroke can have the pump drive/motor 1404 running directly from power supply 40. The retract or fill portion of the cycle or stroke can run at a voltage set by the processing unit 30, so that the retract times are varied by the processing unit 30, where higher desired flow rates require faster retract speeds. The pumping elements 1408, such as the fingers, are operatively associated with the pump drive/motor 1404. When energized, the pumping elements 1408 move to cause pressing on the pumping chamber of the line 1400, and expel fluid therefrom or therethrough. On an up-stroke, pumping elements 1408 release pressure from pumping chamber 1400 and thereby draws fluid into the pumping chamber 1400. Thus, the pumping elements 1408 intermittently pressurize the pumping chamber 1400 during a pumping cycle. The power supply 40, the pump drive/motor 1404, and/or the pumping elements 1408 together, alone, or in some combination thereof, may be considered a pump drive for the purposes of the present specification. Other parts and/or elements may also make up the pump drive, as one of ordinary skill in the art would understand. In addition, parts of each of the power supply 40, the pump drive/motor 1404, the pumping elements 1408, and/or other elements can make up what is referred to herein as the pump drive, with the understanding that the pump drive is controlled by the processing unit 30 for driving the delivery of the substance to the patient through the use of the pumping chamber.

Force/pressure sensors 1412 are each operatively associated with one of the pumping elements 1408 to detect the force or pressure exerted by the pumping element on the pumping chamber 1400. As shown in FIG. 14, the sensors 1412 can be directly connected to the pumping element, and operate to sense the force/pressure on pumping elements 1408 as well as to generate a force/pressure signal based on this force/pressure. The force/pressure sensors 1412 are in electronic communication with the processing unit 30 to send the force/pressure signal to the processing unit 30 for use in determining operating conditions of pump 10, through amplifiers 1416. One of ordinary skill in the art will appreciate that the pressure sensor 1412 may be a force transducer or any other device that can operatively sense the pressure or related force brought to bear on the pumping chamber 1400 by pumping elements 1408.

A position sensor 48 is operatively associated with the pumping element 44 to directly or indirectly detect the position of the pumping elements 1408. The position sensor 48 tracks each pumping cycle of pump 10 by detecting the position of the pumping elements 1408 at each position within each cycle. The position sensor 48 generates a pump drive travel signal by detecting the rotational or linear position of the pump drive/motor 1404. The position sensor 48 is in electronic communication with the processing unit 30 to send the position signal to the processing unit 30. The processing unit 30 utilizes this information in similar ways as described above, such as by associating the incoming force/pressure data with a particular travel value within the delivery, such as a time, a linear distance, and/or rotational distance or angle of travel.

The medical pump 10 of the present invention provides a mechanism for controlling or adjusting the delivery of fluid based on variations from nominal data used to estimate pump performance. The processing unit 30 retrieves the operating condition programming code 36 from memory 34 and applies it to the force/pressure and travel data received during a delivery. The force/pressure data and travel data are processed by the processing unit 30. Sensing the force/pressure, for example that the pumping chamber 1400 exerts against the pumping elements 1408, and analyzing that force/pressure data can determine various parameters for use in the operating the medical pump. The processing unit 30 utilizes these parameters in a closed loop cycle/stroke feedback system to determine and/or calculate delivery parameters.

In one embodiment of the medical pump 10 of FIG. 14, the medical pump 10 can measure the "compliance" of the line, such as a tubing segment, which surrounds the pumping chamber 1400. Specifically, when a unit of force is applied to the tube, the displacement can be measured or determined, or vice versa. Compliance for specific lines, such as tubing segments can be determined as a ratio of this displacement over the applied force. Additionally, the medical pump 10 can apply a constant force value during the pumping cycle, such as a peristaltic cycle. The processing unit 30 and the programming code 36 of the medical pump 10 control the applied force on the tubing line by the pumping elements 1408, and the tubing displacement varies as a function of its compliance. The tubing displacement drives the amount of stroke volume. Thus, the more compliant the tubing segment is, the larger the stroke volume will be for the same amount of applied force by the pumping element(s). The processing unit 30 and programming code 36 use the signals from the force/pressure sensor in a closed-loop manner to control the pump drive and motor movement.

The following describes how a medical pump 10, such as a peristaltic pump, equipped with a position and a force/pressure sensor can control the discharge volume more accurately to achieve improved accuracy and Low Flow Continuity. The medical pump 10 and the processing unit 30, and programming code 36, can use three separate relationships. The first relationship is between the volume displaced during one cycle (stroke volume), such as a peristaltic cycle, and line or tubing compliance. The compliance (displacement per force) for a force/pressure action, such as a peristaltic action, and the stroke volume are measured for a set of line (tubing) samples. The sample set of lines can be selected to represent the population of production tubing statistically. The data can then be used to establish 1) an average stroke volume, 2) an average line (tubing) compliance, 3) a spread in line (tubing) compliance values and 4) a (linear) relationship between the compliance and stroke volume, as follows:

$$Q = \text{Constant} \times \text{Compliance} \quad \text{(Eq. 1)}$$

where,
Q is Volume per Stroke
Constant is Volume×Force per Displacement
Compliance is Displacement per Force This relationship can be established at different temperatures and applied accordingly. The stroke volume for a specific administration line set is therefore determined as a sum of two components: the average component and a delta component.

$$Q(\text{Stroke Volume}) = Q_{average} + Q_{delta}$$

The average component is based on the average stroke volume calculated above for the line population. The delta component, on the other hand, is determined from the compliance of the specific line (tubing). The difference between the compliance of a specific line and average value for the line population is then multiplied by the Constant in Eq. 1, to determine the delta component of the stroke volume ($Q_{delta}$). The stroke volume can therefore be determined for a specific line (tubing). The pump speed (strokes per unit of time) can then be calculated using the stroke volume. For instance, if the stroke volume is 0.07 mL/stroke, and the flow rate is 70 mL/hour, the pump action would have a speed of 1000 strokes/hour.

The second relationship is between the line (tubing) size and compliance. Administration line sets typically use tubing with a 0.138" outside diameter and three nominal inside diameters (IDs): 0.100" macro-bore, 0.05" micro-bore and 0.038" mini-bore. In addition to the average compliance values, the spread in compliance values can also be used to determine the range of compliance values for each line identification (tubing ID). For a specific line, the medical pump 10, and processing unit 30 and programming code 36 therein, would first calculate the compliance to determine the line ID based on the compliance ranges for the three line (tubing) IDs. Furthermore, the pump would have separate relationships described above in Eq. 1 for each line ID to use.

The third relationship is between the discharge volume within a medical pump cycle, such as a peristaltic cycle, and displacement. The non-linear relationship is established for the line population as an average of similar relationships for a statistically significant sample set that represents the population. The relationship can be integrated into the programming code 36 either algebraically or as a look-up table to adjust the number and size of steps at low flow rates to achieve Low Flow Continuity.

It should be emphasized that the above-described embodiments of the present invention are examples of implementations, and are merely set forth for a clear understanding of the principles of the invention. Many variations and modifications may be made to the above-described embodiment(s) of the invention without substantially departing from the spirit and principles of the invention. All such modifications are intended to be included herein within the scope of this disclosure and by the following claims.

What is claimed is:

1. A method for providing low flow continuity of a medical pump having a pump drive and a force/pressure sensor, comprising the steps of:
    determining a cycle start position;

driving the pump drive at a drive rate which is based on a desired delivery rate;

sensing a plurality of force/pressure values over time using the force/pressure sensor, which are representative of the force/pressure exerted on the force/pressure sensor as the driving of the pump drive occurs;

calculating the rate of change of the sensed force/pressure values;

determining in a first determination step whether the rate of change of the sensed force/pressure values meets a first rate of change value;

if the first determination step is true, determining in a second determination step whether the rate of change of the sensed force/pressure values meets a second rate of change value;

if the second determination step is true, calculating a remaining pump drive travel value for determining how much farther the pump drive should travel before the end of an effective pump cycle; and, completing the effective pump cycle delivery using the remaining pump drive travel value.

2. The method of claim 1 further comprising continuously detecting the position of the pump drive.

3. The method of claim 1 wherein the step of calculating the remaining pump drive travel value comprises the steps of:
providing an effective cycle travel value;
determining an already traveled cycle value when the second determination step is true; and,
subtracting the already traveled cycle value from the effective cycle travel value.

4. The method of claim 3 further comprising the step of determining a pump drive step value to complete the effective cycle by dividing the remaining pump drive travel value by a step travel size value.

5. The method of claim 1 wherein the drive rate is selected from a group consisting of a constant rate and a variable rate.

6. The method of claim 1 wherein the first and second rate of change values are both predetermined values, wherein the first determination step comprises determining whether the rate of change of the sensed force/pressure values is greater than the first rate of change value, wherein the second determination step comprises whether the rate of change of the sensed force/pressure values is less than a second rate of change value, and wherein the first rate of change value is less than the second rate of change value.

7. The method of claim 1 further comprising the step of calculating the first and second rate of change values.

8. The method of claim 1 wherein the first and second rate of change values are calculated as predetermined percentages of a highest rate of change value from a previous cycle.

9. The method of claim 1 wherein the pump drive is provided for driving a cam which drives a plunger for exerting a force/pressure within a pumping chamber.

10. The method of claim 1 wherein the cycle comprises a pressurization phase, a pumping phase, and a retraction phase.

11. The method of claim 1 wherein the pump drive is retracted to the cycle start position after a pumping phase is completed.

12. The method of claim 1 wherein the step of calculating the predetermined drive rate to drive the pump drive is based on a cycle calibration value.

13. The method of claim 1 further comprising the step of determining whether the pump drive has traveled beyond a minimum allowable pump drive travel value for a cycle.

14. The method of claim 1 further comprising the step of determining whether the pump drive has traveled beyond a maximum allowable pump drive travel value for a cycle.

15. The method of claim 1 further comprising the steps of:
storing the plurality of sensed force/pressure values; and,
calculating an average force/pressure value for each of a plurality of time intervals, and using the averaged force/pressure values to determine the rate of change of the sensed force/pressure values.

16. The method of claim 1 further comprising the steps of:
determining whether a predetermined initial travel value has been met in relation to the cycle start position; and,
preventing at least one of the following steps until the predetermined initial travel value has been met:
a) the first determination step;
b) the step of sensing the plurality of force/pressure values;
c) the step of calculating the rate of change of the sensed force/pressure values; and/or,
d) the step of calculating the remaining pump drive travel value.

17. The method of claim 1 further comprising the steps of:
determining whether an additional travel value has been met after the first determination step is true; and,
preventing at least one of the following steps until the additional travel value has been met:
a) the second determination step;
b) the step of sensing the plurality of force/pressure values;
c) the step of calculating the rate of change of the sensed force/pressure values; and/or,
d) the step of calculating the remaining pump drive travel value.

18. A method for providing low flow continuity of a medical pump having a pump drive and a force/pressure sensor, comprising the steps of:
determining a cycle start position;
driving the pump drive at a drive rate which is based on a desired delivery rate;
sensing a plurality of force/pressure values over time using the force/pressure sensor, which are representative of the force/pressure exerted on the force/pressure sensor as the driving of the pump drive occurs;
determining whether a predetermined initial travel value has been met in relation to the cycle start position;
calculating the rate of change of the sensed force/pressure values;
if the rate of change of the sensed force/pressure values is less than the threshold rate of change value, calculating a remaining pump drive travel value for determining how much farther the pump drive should travel before the end of an effective pump cycle;
preventing at least one of the following steps until a predetermined initial travel value has been met:
a) sensing the plurality of force/pressure values;
b) calculating the rate of change of the sensed force/pressure values;
determining whether the rate of change of the sensed force/pressure values is less than a threshold rate of change value; and/or,
c) calculating the remaining pump drive travel value; and,
completing the effective pump cycle delivery using the remaining pump drive travel value.

19. The method of claim 16 wherein the initial travel value is selected from a group consisting of a time and a distance.

20. A method for providing low flow continuity of a medical pump having a pump drive and a force/pressure sensor, comprising the steps of:
determining a cycle start position;

driving the pump drive at a drive rate which is based on a desired delivery rate;
sensing a plurality of force/pressure values using the force/pressure sensor, which are representative of the force/pressure exerted on the force/pressure sensor as the driving of the pump drive occurs;
calculating the rate of change of the sensed force/pressure values;
determining whether the rate of change of the sensed force/pressure values has met a threshold rate of change value;
if the rate of change of the sensed force/pressure values has met the threshold rate of change value, then at least one of determining whether a predetermined further travel value has been met and/or driving the pump drive based on the predetermined further travel value;
if the predetermined further travel value has been met and/or fulfilled, then calculating a remaining pump drive travel value for determining how much farther the pump drive should travel before the end of an effective pump cycle; and,
completing the effective pump cycle delivery using the remaining pump drive travel value.

21. A method for providing low flow continuity of a medical pump having a pump drive and a force/pressure sensor, comprising the steps of:
determining a delivery cycle start position;
determining the amount of a substance remaining to be delivered;
driving the pump drive at a drive rate which is based on a desired delivery rate;
sensing a plurality of force/pressure values over a travel distance using the force/pressure sensor, which are representative of the force/pressure exerted on the force/pressure sensor as the driving of the pump drive occurs;
determining the rate of change of the sensed force/pressure values over the travel distance;
determining in a first determination step whether the rate of change of the sensed force/pressure values meets a first rate of change value;
if the first determination step is true, determining whether the amount of the substance remaining to be delivered has changed; and,
if the amount of the substance remaining to be delivered has changed more than a change threshold, completing the delivery cycle.

22. The method of claim 21 wherein the amount of the substance is selected from a group consisting of a weight and a volume.

23. The method of claim 21 further comprising the step of:
if the amount of the substance remaining has not changed more than the change threshold, then driving the pump drive in a reverse direction for unsticking the substance delivery.

24. The method of claim 23 further comprising the step of:
if the amount of the substance remaining has not changed more than the change threshold, then alternating the driving of the pump drive in a forward direction and the reverse direction a plurality of times within a time interval for unsticking the substance delivery.

25. The method of claim 21 further comprising the steps of:
determining in a second determination step whether the rate of change of the sensed force/pressure values meets a second rate of change value; and,
if the second determination step is true, determining whether the amount of the substance remaining to be delivered has changed.

26. A method for providing low flow continuity of a medical pump having a pump drive and a force/pressure sensor, comprising the steps of:
determining a cycle start position;
driving the pump drive at a drive rate which is based on a desired delivery rate;
sensing a plurality of force/pressure values using the force/pressure sensor, which are representative of the force/pressure exerted on the force/pressure sensor as the driving of the pump drive occurs;
determining a delivery start position by calculating the rate of change of the sensed force/pressure values and determining the delivery start position when a rate of change threshold has been met;
calculating the remaining pump drive travel value in relation to the delivery start position, comprising the steps of:
receiving an effective cycle travel value;
determining an already traveled cycle value based on the delivery start position; and,
subtracting the already traveled cycle value from the effective cycle travel value; and,
driving the pump drive using the remaining pump drive travel value.

27. A medical pump for low flow delivery of a substance, for use with a pumping chamber, comprising:
a pump drive for exerting a force on the pumping chamber;
a sensor operatively associated with the pump drive for sensing the force/pressure exerted by the pump drive on the pumping chamber;
a pump drive position sensor operatively connected to the pump drive for sensing the position of the pump drive;
a processor in electronic communication with the pump drive, the force/pressure sensor, and the pump drive position sensor;
a memory in electronic communication with the processor, wherein the memory comprises programming code for execution by the processor, and wherein the programming code is adapted to:
calculate the rate of change of the sensed force/pressure values over time;
determine in a first determination step whether the rate of change of the sensed force/pressure values meets a first rate of change value;
if the first determination step is true, determine in a second determination step whether the rate of change of the sensed force/pressure values meets than a second rate of change value;
if the second determination step is true, calculate a remaining pump drive travel value for determining how much farther the pump drive should travel before the end of an effective pump cycle; and,
trigger a plurality of pump drive signals for driving the pump drive for the remainder of the effective pump cycle using the remaining pump drive travel value.

28. The medical pump of claim 27, wherein the pump drive comprises a stepper motor, and wherein the programming code is further adapted to determine a motor step size value for driving the stepper motor according to the motor step size value.

29. The medical pump of claim 27, wherein the pump drive comprises a stepper motor, and wherein the programming code is further adapted to receive a set motor RPM value for use in calculating the remaining pump drive travel value.

30. The medical pump of claim 27, wherein the programming code is further adapted to calculate an estimated incremental delivery volume.

31. The medical pump of claim 27, wherein the pump drive drives a pumping element for exerting a force on the pumping chamber.

32. The medical pump of claim 27, wherein the pumping chamber is a portion of at least one of a cassette, a tube, and/or a syringe.

33. The medical pump of claim 27 wherein the pump drive position sensor has a resolution of from about 0.15 mils to about 0.45 mils.

34. A medical pump for low flow delivery of a substance, for use with a pumping chamber, comprising:
- a pump drive for exerting a force on the pumping chamber;
- a sensor operatively associated with the pump drive for sensing the force/pressure exerted by the pump drive on the pumping chamber;
- a pump drive position sensor operatively connected to the pump drive for sensing the position of the pump drive;
- a processor in electronic communication with the pump drive, the force/pressure sensor, and the pump drive position sensor;
- a memory in electronic communication with the processor, wherein the memory comprises programming code for execution by the processor, and wherein the programming code is adapted to:
- determine a cycle start position;
- calculate the rate of change of the sensed force/pressure values;
- determine whether a predetermined initial travel value has been met in relation to the cycle start position;
- prevent at least one of the following steps until the predetermined initial travel value has been met:
  a) sense the plurality of force/pressure values; and/or,
  b) calculate the rate of change of the sensed force/pressure values;
- determine whether the rate of change of the sensed force/pressure values is less than a threshold rate of change value;
- if the rate of change of the sensed force/pressure values is less than the threshold rate of change value, calculate a remaining pump drive travel value for determining how much farther the pump drive should travel before the end of an effective pump cycle; and,
- trigger a plurality of pump drive signals for driving the pump drive for the remainder of the effective pump cycle using the remaining pump drive travel value.

35. A medical pump for low flow delivery of a substance, for use with a pumping chamber, comprising:
- a pump drive for exerting a force on the pumping chamber;
- a sensor operatively associated with the pump drive for sensing the force/pressure exerted by the pump drive on the pumping chamber;
- a pump drive position sensor operatively connected to the pump drive for sensing the position of the pump drive;
- a processor in electronic communication with the pump drive, the force/pressure sensor, and the pump drive position sensor;
- a memory in electronic communication with the processor, wherein the memory comprises programming code for execution by the processor, and wherein the programming code is adapted to:
- determine a cycle start position;
- calculate the rate of change of the sensed force/pressure values;
- determine whether the rate of change of the sensed force/pressure values has met a threshold rate of change value;
- if the rate of change of the sensed force/pressure values has met the threshold rate of change value, then at least one of determine whether a predetermined further travel value has been met and/or drive the pump drive based on the predetermined further travel value;
- if the predetermined further travel value has been met or fulfilled, then calculate a remaining pump drive travel value in order to determine how much farther the pump drive should travel before the end of an effective pump cycle; and,
- trigger a plurality of pump drive signals for driving the pump drive for the remainder of the effective pump cycle using the remaining pump drive travel value.

36. A medical pump for low flow delivery of a substance, for use with a pumping chamber, comprising:
- a pump drive for exerting a force on the pumping chamber;
- a sensor operatively associated with the pump drive for sensing the force/pressure exerted by the pump drive on the pumping chamber;
- a pump drive position sensor operatively connected to the pump drive for sensing the position of the pump drive;
- a processor in electronic communication with the pump drive, the force/pressure sensor, and the pump drive position sensor;
- a memory in electronic communication with the processor, wherein the memory comprises programming code for execution by the processor, and wherein the programming code is adapted to:
- receive a delivery cycle start position;
- determine the amount of the substance remaining to be delivered;
- determine the rate of change of the sensed force/pressure values over the travel distance;
- determine in a first determination step whether the rate of change of the sensed force/pressure values meets a first rate of change value;
- if the first determination step is true, determine whether the amount of the substance remaining to be delivered has changed; and,
- if the amount of the substance remaining to be delivered has changed more than a change threshold, trigger a plurality of pump drive signals for driving the pump drive for the remainder of the effective pump cycle using the remaining pump drive travel value.

37. A medical pump for low flow delivery of a substance, for use with a pumping chamber, comprising:
- a pump drive for exerting a force on the pumping chamber;
- a sensor operatively associated with the pump drive for sensing the force/pressure exerted by the pump drive on the pumping chamber;
- a pump drive position sensor operatively connected to the pump drive for sensing the position of the pump drive;
- a processor in electronic communication with the pump drive, the force/pressure sensor, and the pump drive position sensor;
- a memory in electronic communication with the processor, wherein the memory comprises programming code for execution by the processor, and wherein the programming code is adapted to:
- receive a cycle start position;
- determine a delivery start position by calculating the rate of change of the sensed force/pressure values and determine the delivery start position when a rate of change threshold has been met;
- calculate the remaining pump drive travel value in relation to the delivery start position, comprising the steps of:

receive an effective cycle travel value representative of an effective cycle travel;
determine an already traveled cycle value based on the delivery start position; and,
subtract the already traveled cycle value from the effective cycle travel value; and,
trigger a plurality of pump drive signals for driving the pump drive for the remainder of the effective cycle travel using the remaining pump drive travel value.

38. A medical pump for low flow delivery of a substance, for use with a pumping chamber, comprising:
a pump drive for exerting a force on the pumping chamber;
a sensor operatively associated with the pump drive for sensing the force/pressure exerted by the pump drive on the pumping chamber;
a pump drive position sensor operatively connected to the pump drive for sensing the position of the pump drive;
a processor in electronic communication with the pump drive, the force/pressure sensor, and the pump drive position sensor;
a memory in electronic communication with the processor, wherein the memory comprises programming code for execution by the processor, and wherein the programming code is adapted to:
calculate the rate of change of the sensed force/pressure values;
determine in a first determination step whether the rate of change of the sensed force/pressure values meets a first rate of change value;
if the first determination step is true, at least one of calculate a remaining pump drive travel value and/or determine whether the amount of the substance remaining to be delivered has changed; and,
trigger a plurality of pump drive signals for driving the pump drive for the remainder of the effective pump cycle.

39. The medical pump of claim 38 wherein calculating a remaining pump drive travel value is performed for determining how much farther the pump drive should travel before the end of an effective pump cycle.

40. The medical pump of claim 38 wherein the step of triggering the plurality of pump drive signals uses the remaining pump drive travel value to trigger the plurality of pump drive signals.

41. The medical pump of claim 38 wherein the programming code is further adapted to:
receive a delivery cycle start position;
determine the amount of the substance remaining to be delivered; and,
if the amount of the substance remaining to be delivered has changed more than a change threshold, trigger the plurality of pump drive signals for driving the pump drive for the remainder of the effective pump cycle using the remaining pump drive travel value.

* * * * *